United States Patent
Yamada et al.

(10) Patent No.: US 11,370,733 B2
(45) Date of Patent: Jun. 28, 2022

(54) ORGANIC COMPOUND, ORGANIC LIGHT-EMITTING ELEMENT, DISPLAY DEVICE, IMAGING DEVICE, ELECTRONIC DEVICE, ILLUMINATION DEVICE, AND MOVING OBJECT

(71) Applicant: CANON KABUSHIKI KAISHA, Tokyo (JP)

(72) Inventors: Naoki Yamada, Inagi (JP); Jun Kamatani, Tokyo (JP); Yosuke Nishide, Kawasaki (JP); Hirokazu Miyashita, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 365 days.

(21) Appl. No.: 16/534,471

(22) Filed: Aug. 7, 2019

(65) Prior Publication Data
US 2020/0048171 A1    Feb. 13, 2020

(30) Foreign Application Priority Data
Aug. 10, 2018 (JP) .............................. JP2018-152006

(51) Int. Cl.
*C07C 13/62* (2006.01)
*H01L 51/00* (2006.01)
(Continued)

(52) U.S. Cl.
CPC .............. *C07C 13/62* (2013.01); *C07C 25/22* (2013.01); *C07C 255/52* (2013.01);
(Continued)

(58) Field of Classification Search
None
See application file for complete search history.

(56) References Cited

U.S. PATENT DOCUMENTS
2013/0048966 A1    2/2013 Horiuchi

FOREIGN PATENT DOCUMENTS
JP    2013-043846 A    3/2013
WO    2011/152477 A1    12/2011

*Primary Examiner* — Jay Yang
(74) *Attorney, Agent, or Firm* — Canon U.S.A., Inc., IP Division

(57) ABSTRACT

An organic compound that emits red light having a long wavelength is represented by formula (1). In formula (1), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

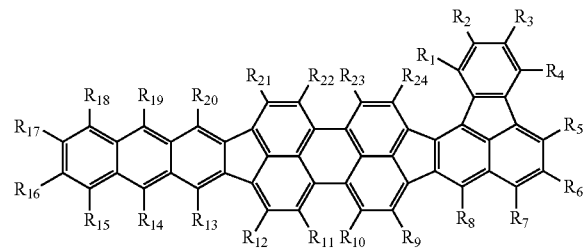

17 Claims, 7 Drawing Sheets

(51) Int. Cl.
*C09K 11/06* (2006.01)
*C07C 25/22* (2006.01)
*C07D 213/06* (2006.01)
*C07C 255/52* (2006.01)
*H01L 27/32* (2006.01)
*H01L 51/50* (2006.01)
*H01L 51/52* (2006.01)

(52) U.S. Cl.
CPC ............ *C07D 213/06* (2013.01); *C09K 11/06* (2013.01); *H01L 51/0056* (2013.01); *H01L 51/0058* (2013.01); *H01L 51/0067* (2013.01); *C07C 2603/54* (2017.05); *C09K 2211/1007* (2013.01); *C09K 2211/1011* (2013.01); *C09K 2211/1018* (2013.01); *H01L 27/322* (2013.01); *H01L 27/3234* (2013.01); *H01L 27/3244* (2013.01); *H01L 51/0097* (2013.01); *H01L 51/504* (2013.01); *H01L 51/5268* (2013.01); *H01L 2251/5338* (2013.01); *H01L 2251/5361* (2013.01)

ORGANIC COMPOUND, ORGANIC LIGHT-EMITTING ELEMENT, DISPLAY DEVICE, IMAGING DEVICE, ELECTRONIC DEVICE, ILLUMINATION DEVICE, AND MOVING OBJECT

BACKGROUND OF THE INVENTION

Field of the Invention

The present disclosure relates to an organic compound and an organic light-emitting element having a high color purity, a display device, an imaging device, an electronic device, an illumination device, and a moving object that use the organic compound.

Description of the Related Art

An organic light-emitting element (also referred to as an "organic electroluminescence element" or "organic EL element") is an electronic element including a pair of electrodes and an organic compound layer disposed between the electrodes. Electrons and holes are injected from the pair of electrodes to thereby generate excitons of a luminescent organic compound in the organic compound layer. The organic light-emitting element emits light when the excitons return to their ground state.

Recently, there has been remarkable progress in organic light-emitting elements. For example, it is possible to realize a low driving voltage, various emission wavelengths, high-speed response, and reductions in the thickness and weight of a light-emitting device.

The standards of sRGB and AdobeRGB are used as a color reproduction range used in displays, and materials that reproduce such colors have been desired. Recently, BT-2020 has been proposed as a standard that further extends the color reproduction range.

Compounds having good light-emitting properties have been actively created to date. Japanese Patent Laid-Open No. 2013-043846 (hereinafter referred to as PTL 1) discloses a compound 1-A represented by the following structural formula.

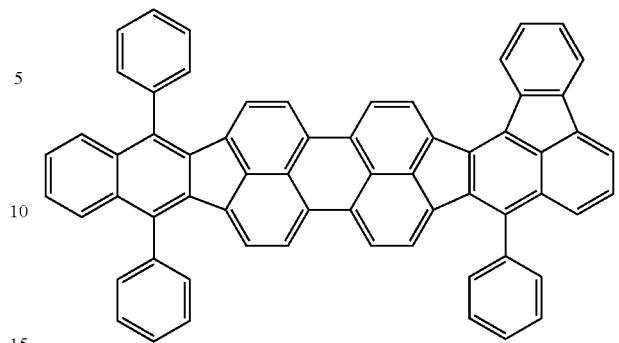

An organic light-emitting element that uses the compound described in PTL 1 may be difficult to reproduce chromaticity coordinates (0.71, 0.29) of red in the color reproduction range of BT-2020. Thus, a compound that emits red light at a longer wavelength has been desired. It is known that a longer emission wavelength of an organic compound can be realized by providing a substituent. However, providing a substituent for changing the wavelength is not preferred because stability of the organic compound may decrease.

SUMMARY OF THE INVENTION

The present disclosure provides an organic compound having a basic skeleton that emits red light having a longer wavelength.

An organic compound according to an embodiment of the present disclosure is represented by formula (1).

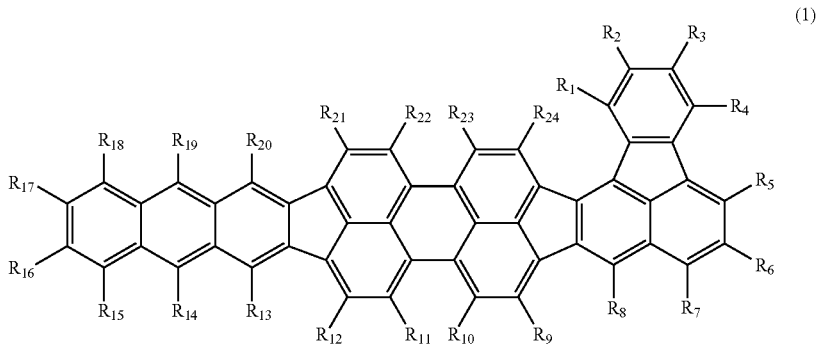

(1)

In formula (1), $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

Further features of the present disclosure will become apparent from the following description of exemplary embodiments with reference to the attached drawings.

DESCRIPTION OF THE EMBODIMENTS

Figure 1:
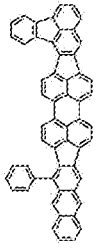
FIG. 1 includes structural formulae of molecules.

An organic compound according to the present embodiment is an organic compound represented by general formula (1) below. The organic compound represented by general formula (1) is also referred to as an organic compound according to the present embodiment or an organic compound according to the present disclosure.

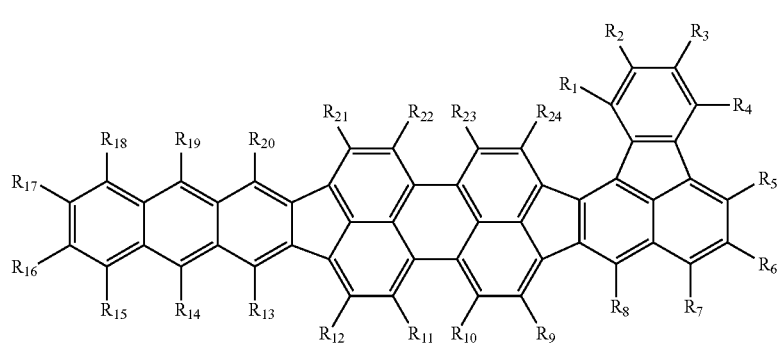

In general formula (1), $R_1$ to $R_{24}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

In the present embodiment, $R_1$ to $R_{24}$ in general formula (1) are each preferably independently selected from a hydrogen atom, a substituted or unsubstituted alkyl group, and a substituted or unsubstituted aryl group.

Examples of the halogen atom represented by $R_1$ to $R_{24}$ include, but are not limited to, fluorine, chlorine, bromine, and iodine.

Examples of the alkyl group represented by $R_1$ to $R_{24}$ include alkyl groups having 1 to 10 carbon atoms. More specifically, examples thereof include, but are not limited to, a methyl group, an ethyl group, a normal propyl group, an isopropyl group, a normal butyl group, a tertiary butyl group, a secondary butyl group, an octyl group, a cyclohexyl group, a 1-adamantyl group, and a 2-adamantyl group.

Examples of the alkoxy group represented by $R_1$ to $R_{24}$ include alkoxy groups having 1 to 10 carbon atoms. More specifically, examples thereof include, but are not limited to, a methoxy group, an ethoxy group, a propoxy group, a 2-ethyl-octyloxy group, and a benzyloxy group.

Examples of the amino group represented by $R_1$ to $R_{24}$ include amino groups having an alkyl group or an aryl group as a substituent. The amino group may have two alkyl groups, two aryl groups, or an alkyl group and an aryl group. In particular, the amino group preferably has two aryl groups. More specifically, examples thereof include, but are not limited to, an N-methylamino group, an N-ethylamino group, an N,N-dimethylamino group, an N,N-diethylamino group, an N-methyl-N-ethyl amino group, an N-benzylamino group, an N-methyl-N-benzylamino group, an N,N-dibenzylamino group, an anilino group, an N,N-diphenylamino group, an N,N-dinaphthylamimo group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tertiary butylphenyl)amino group, an N-phenyl-N-(4-trifluoromethylphenyl)amino group, and an N-piperidyl group.

Examples of the aryl group represented by $R_1$ to $R_{24}$ include aryl groups having 6 to 18 carbon atoms. More specifically, examples thereof include, but are not limited to, a phenyl group, a naphthyl group, an indenyl group, a biphenyl group, a terphenyl group, and a fluorenyl group, a phenanthryl group, and a triphenylenyl group.

Examples of the heterocyclic group represented by $R_1$ to $R_{24}$ include heterocyclic groups having 3 to 15 carbon atoms. More specifically, examples thereof include, but are not limited to, a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group.

Examples of the aryloxy group represented by $R_1$ to $R_{24}$ include, but are not limited to, a phenoxy group and a thienyloxy group.

Examples of the silyl group represented by $R_1$ to $R_{24}$ include, but are not limited to, a trimethylsilyl group and a triphenylsilyl group.

Examples of the substituents that may be further contained in the alkyl group, the alkoxy group, the amino group, the aryl group, the heterocyclic group, and the aryloxy group include, but are not limited to, alkyl groups such as a methyl group, an ethyl group, a normal propyl group, an isopropyl group, a normal butyl group, and a tertiary butyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenyl amino group, and a ditolylamino group; alkoxy groups such as a methoxy group, an ethoxy group, and a propoxy group; aryloxy groups such as a phenoxy group, halogen atoms such as fluorine, chlorine, bromine, and iodine; and a cyano group.

In the present embodiment, $R_1$ to $R_{24}$ in general formula (1) are each preferably independently selected from a hydrogen atom and substituted or unsubstituted aryl groups.

Herein, the basic skeleton is a structure in which $R_1$ to $R_{24}$ of the compound represented by general formula (1) above are each a hydrogen atom.

Next, a method for synthesizing an organic compound according to the present embodiment will be described. The organic compound according to the present embodiment is synthesized in accordance with, for example, the following reaction scheme.

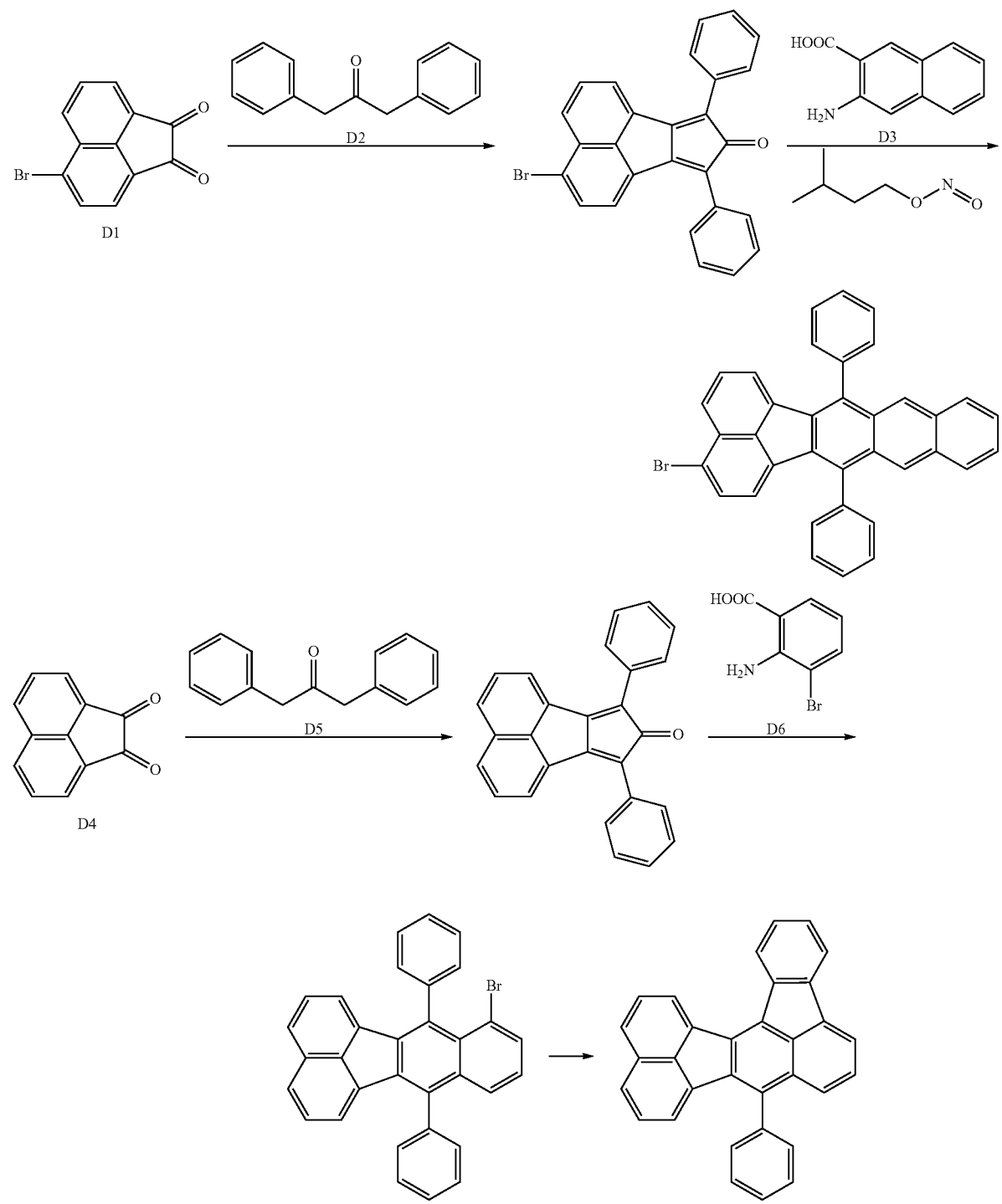

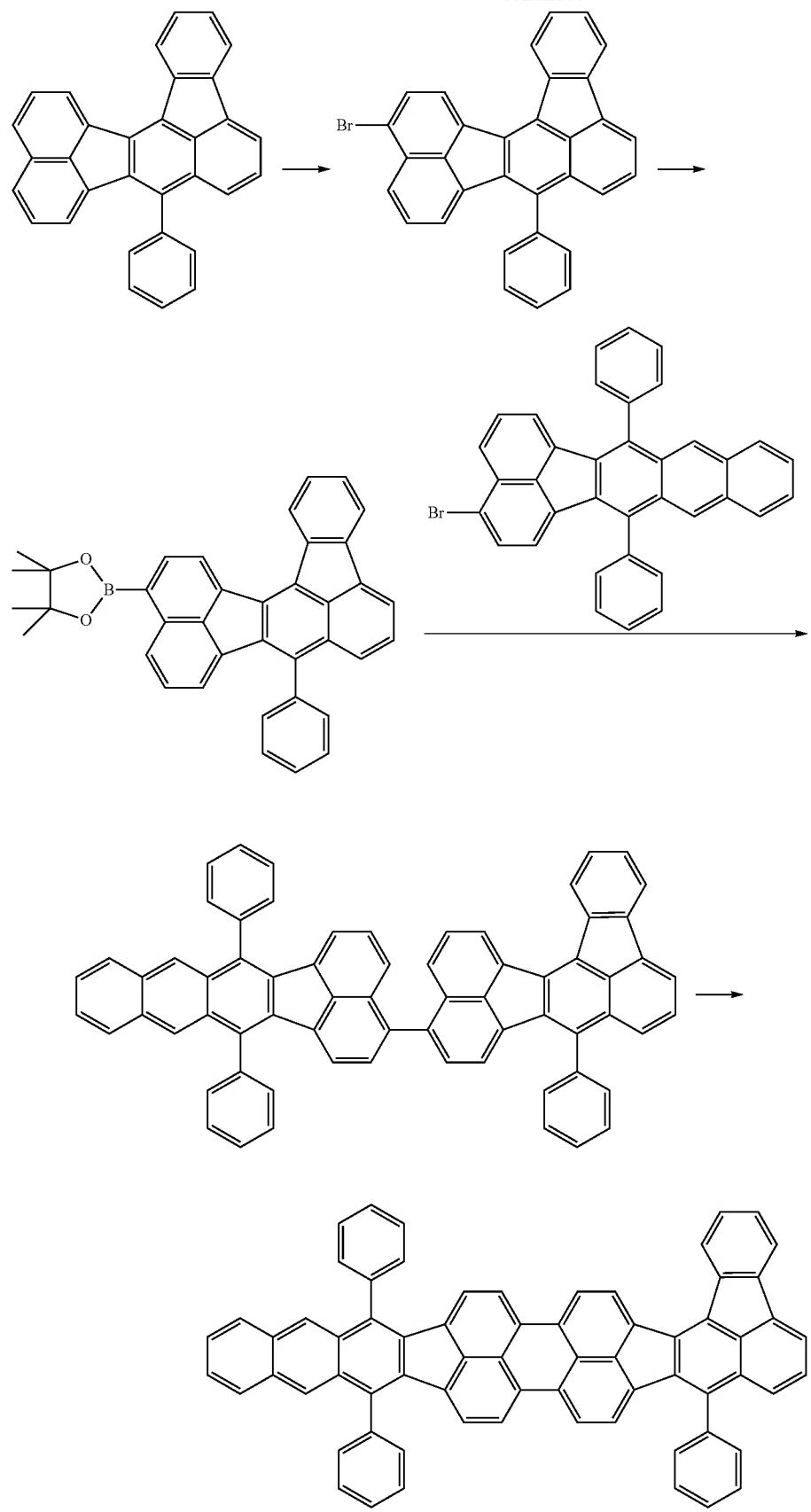

As shown by the above synthesis scheme, the organic compound according to the present embodiment is synthesized by using the compounds represented by (a) to (d) below.

(a) Acenaphthenequinone derivatives (D1) and (D4)
(b) Dibenzyl ketone derivatives (D2) and (D5)
(c) Naphthalene anthranilic acid derivative (3-Amino-2-naphthoic acid derivative) (D3)
(d) Benzene anthranilic acid derivative (2-Aminobenzoic acid derivative) (D6)

Desired organic compounds represented by general formula (1) can be obtained by appropriately providing substituents to the compounds represented by (a) to (d) above.

The organic compound according to the present embodiment is a stable organic compound that emits red light having a high color purity because of the following features.

(i) The emission wavelength of the basic skeleton itself is in a long-wavelength red range.
(ii) The structure of the basic skeleton consists of elements of a hydrocarbon.
(iii) The quantum yield is high because of a high transition dipole moment.

Hereafter, these features will be described.

In the present embodiment, calculated values of the molecular structure, HOMO, the oscillator strength, the dihedral angle, and the binding energy were determined by using the following molecular orbital calculations. The HOMO is an abbreviation of "highest occupied molecular orbital" and represents the energy level of the highest occupied molecular orbital.

The density functional theory (DFT), which has been currently widely used, was used as a calculation technique of the molecular orbital calculations. The B3LYP was used as the functional, and the 6-31G* was used as the basis function. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.), which has been currently widely used.

(i) The emission wavelength of the basic skeleton itself is in a long-wavelength red range.

In the creation of the organic compound represented by general formula (1), the inventors of the present disclosure focused on the basic skeleton itself. Specifically, the molecule was designed so that the wavelength of light emitted due to the basic skeleton is within a desired wavelength range.

In the present embodiment, the desired wavelength range is a red range. Specifically, the maximum peak wavelength is in a range of 610 nm or more and 640 nm or less in a dilute solution.

The emission wavelength range of the organic compound according to the present embodiment will be described while comparing with a reference compound having a structure similar to that of the organic compound according to the present embodiment. Here, the reference compound is comparative compound 1-A which is a compound described in PTL 1 and shown in Table 1 below. The comparison of the emission wavelength was conducted by using compounds each having three phenyl groups in addition to a basic skeleton. The reason for this is to reduce the effect of concentration quenching by suppressing stacking of the molecules. Since the phenyl groups are located at substitution positions at which the effect on the conjugation is small, the phenyl groups do not significantly affect the emission wavelength. That is, light emission close to the light emission caused by the basic skeleton itself is achieved.

The inventors of the present disclosure compared the emission wavelength between comparative compound 1-A and exemplary compound A3 according to the present embodiment. Table 1 shows the results. The measurement of the emission wavelength was conducted by photoluminescence measurement of a diluted toluene solution at an excitation wavelength of 350 nm at room temperature using a fluorescence spectrophotometer F-4500 manufactured by Hitachi, Ltd.

TABLE 1

| | Structural formula | Maximum peak wavelength |
|---|---|---|
| Comparative compound 1-A | | 607 nm |

TABLE 1-continued

| | Structural formula | Maximum peak wavelength |
|---|---|---|
| Exemplary compound A3 | (structure) | 628 nm |

Referring to Table 1, the emission color of comparative compound 1-A is red but is not in the desired wavelength range. Specifically, the color purity in comparative compound 1-A is lower than that in the organic compound according to the present embodiment. In contrast, since exemplary compound A3 has a maximum peak wavelength in the desired range, exemplary compound A3 exhibits a long-wavelength red emission color suitable for red in a display standard such as BT-2020. The basic skeleton of the organic compound according to the present embodiment can exhibits light emission having a high color purity and capable of reproducing deep red. Chromaticity coordinates of red will be described in detail in Examples.

(ii) The structure of the basic skeleton consists of elements of a hydrocarbon.

The compound represented by general formula (1) according to the present embodiment has a basic skeleton consisting of a hydrocarbon. The substituents are also preferably those consisting of hydrocarbons. Regarding the realization of a longer emission wavelength, a longer emission wavelength of a compound may be realized by using the effect of an electron-donating property, for example, by bonding an amino group or the like in a molecular structure. However, when a compound having an unstable bond with a low binding energy, such as an amino group, is used as a luminescent material that forms an organic EL element, the compound is likely to deteriorate during the operation of the element and is highly likely to adversely affect the durability of the organic EL element.

In contrast, the compound represented by general formula (1) according to the present embodiment is a compound consisting of a hydrocarbon and thus has a high binging energy. Accordingly, when the compound represented by general formula (1) is used in an organic EL element, the organic EL element has high durability.

For example, referring to compounds A-1, A-2, and B-1 shown below, the bond having low binding stability is the bond linking a carbazole ring to a phenyl group and the bond linking an amino group to a phenyl group (nitrogen-carbon bonds). The bond linking carbon to carbon as shown in compound B-1 has higher binding stability than the above bonds.

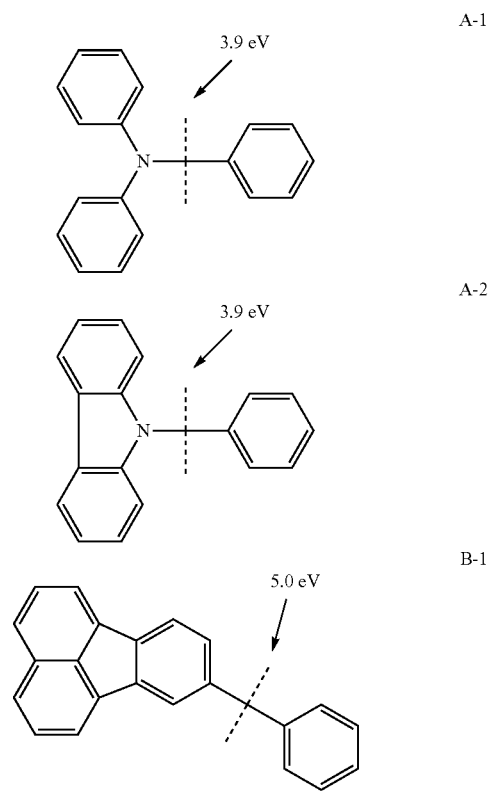

(iii) The quantum yield is high because of a high transition dipole moment.

In expansion of the basic skeleton for realizing a longer wavelength, the inventors of the present disclosure focused on the positions at which benzene rings are condensed. To realize a longer wavelength for comparative compound 1-A described in PTL 1, various positions are conceivable as the positions at which benzene rings are condensed. It has been found that, in particular, as shown in exemplary compound A3, when benzene rings are condensed in a direction in which the molecule has the longest length with respect to the molecular axis, a significant effect due to a longer wavelength is obtained, and the oscillator strength that affects the quantum yield is high.

The basic skeleton of general formula (1) according to the present embodiment has a transition dipole moment in the direction in which the molecule has the longest length with respect to the molecular axis. In condensation of benzene rings, a high effect of increasing the transition dipole moment is obtained when the benzene rings are condensed so as to extend the length in this direction.

These features will be described below.

(iv) The organic compound has a bulky substituent at any of $R_8$, $R_{13}$, $R_{14}$, $R_{19}$, and $R_{20}$.

When the organic compound according to the present embodiment further has a substituent on the basic skeleton, crystallinity of the molecule itself due to intermolecular stacking can be reduced. The reduction in crystallinity leads

TABLE 2

| | Structural formula | Maximum emission wavelength | Oscillator strength (Calculated value) |
|---|---|---|---|
| Comparative compound 1-A | | 607 nm | 1.17 |
| Exemplary compound A3 | | 628 nm | 1.29 |

Furthermore, organic compounds that satisfy conditions (iv) and (v) described below are preferred as compounds used in an organic light-emitting element. This is because when the conditions (iv) and (v) are satisfied, the effect of suppressing intermolecular stacking is enhanced, and improvement in sublimability and suppression of concentration quenching can be realized. The improvement in sublimability can realize a higher purity of a material by sublimation purification and preparation of an organic light-emitting element by vapor deposition. As a result, impurities contained in the organic light-emitting element can be reduced to suppress a decrease in the light emission efficiency due to impurities and a decrease in driving durability. The suppression of concentration quenching is preferred from the viewpoint of improving the light emission efficiency of the organic light-emitting element.

(iv) The organic compound has a bulky substituent at any of $R_8$, $R_{13}$, $R_{14}$, $R_{19}$, and $R_{20}$.

(v) The organic compound has such a substituent that covers a molecular plane.

to suppression of concentration quenching between molecules and improvement in sublimability.

The organic compound according to the present embodiment has a basic skeleton having high planarity. Accordingly, intermolecular stacking tends to occur when the organic compound has no substituents. Substitution positions in this basic skeleton capable of effectively suppressing the intermolecular stacking will be described.

Table 3 shows the result of a calculated dihedral angle between the basic skeleton and a phenyl group, the degree of twist estimated from the dihedral angle, and the magnitude of steric repulsion when a position of the structure represented by general formula (1) according to the present embodiment is substituted with a phenyl group.

In the cases of the substituent patterns 1 to 3, the twist of the phenyl group is large due to a large steric repulsion between hydrogen atoms at the ortho positions of the phenyl group and hydrogen atoms of the basic skeleton. Therefore, the planarity of the whole molecule is lost. This effect suppresses the intermolecular stacking and reduces crystallinity, resulting in the suppression of concentration quenching between molecules and the improvement in sublimability.

TABLE 3

| | Structural formula | Steric repulsion | Twist of substituent | Dihedral angle |
|---|---|---|---|---|
| Substituent pattern 1 | | Large | Large | 90.1 degrees |
| Substituent pattern 2 | | Large | Large | 90.8 degrees |
| Substituent pattern 3 | | Large | Large | 89.9 degrees |
| Substituent pattern 4 | | Small | Small | 37.1 degrees |
| Substituent pattern 5 | | Small | Small | 39.4 degrees |

(v) The organic compound has such a substituent that covers a molecular plane.

In the present embodiment, when the substituent is an alkyl group, for example, a methyl group, an ethyl group, a propyl group, a butyl group, a hexyl group, and an octyl group are preferred. An isopropyl group and a tertiary butyl group, which are sterically bulky, are particularly preferred. When the substituent is an aryl group, aryl groups such as a phenyl group and a naphthyl group are preferred, a phenyl group, which has a low molecular weight, is more preferred from the viewpoint of sublimability, and an aryl group such as a phenyl group having a substituent, such as a methyl group, an isopropyl group, or a tertiary butyl, is particularly preferred. Halogen-substituted aryl groups are also preferred from this viewpoint. The substituting halogen is preferably a fluorine atom.

The substituent is preferably introduced because when the organic compound is used in a method including dissolving the organic compound in a solvent, disposing the resulting solution at a predetermined position or applying the resulting solution, and subsequently removing the solvent, properties of the resulting film improve.

Furthermore, the substituent is preferably disposed so as to overlap the π-conjugated plane in plan view. Specifically, as shown in FIG. 1, an ortho-tolyl compound having a methyl group at an ortho-position of a phenyl group and an ortho-biphenyl compound having a phenyl group at an ortho-position of a phenyl group are preferred because the substituent covers the π-conjugated plane of the basic skeleton, and intermolecular stacking can be suppressed. A phenyl group can effectively suppress intermolecular stacking compared with a methyl group. The plan view means a plan view when viewed from a direction perpendicular to the plane of the basic skeleton. FIG. 1 shows the structural formula of a molecule, a molecular plane direction 1, and a molecular plane direction 2. The structural formula of a molecule is a chemical structure formula of each compound.

The molecular plane direction 1 shows a molecule when the structure represented by the structural formula is observed from the left side of the page of FIG. 1. The molecule is observed from a viewpoint parallel to the main plane of the molecular structure. The molecular plane direction 2 shows a molecule when the structure represented by the structural formula is observed from the lower side of the page of FIG. 1. The observation from the molecular plane directions shows that the substituent is disposed at a large angle with respect to the molecular plane.

Accordingly, when the organic compound according to the present embodiment satisfies the condition (v), an organic compound in which molecular stacking is suppressed and which has high sublimability is provided.

Table 4 shows exemplary compounds A3, C2, and D2, which are compounds according to the present disclosure. Table 4 shows a decrease in the sublimation temperature of C2 and D2 with respect to the decrease in the sublimation temperature of A3. In C2 substituted with an ortho-tolyl group and D2 substituted with an ortho-biphenyl group, the groups covering the π-conjugated plane, the sublimation temperature is decreased relative to A3 in which the basic skeleton is substituted with a phenyl group. The sublimation temperature is a sublimation start temperature when a compound is sublimated by increasing a temperature at a degree of vacuum of $1.0 \times 10^{-2}$ Pa or less. Note that the sublimation temperature of A3 is also decreased compared with that of the basic skeleton itself, and thus sublimability improves.

TABLE 4

| Exemplary compound | Structural formula | Decrease in sublimation purification temperature |
|---|---|---|
| A3 | | — |
| C2 | | −10° C. |

TABLE 4-continued

| Exemplary compound | Structural formula | Decrease in sublimation purification temperature |
|---|---|---|
| D2 | 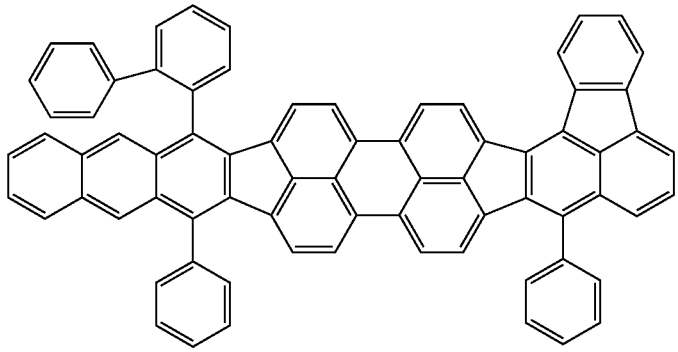 [SMILES: c1ccc(-c2ccccc2-c2c3c(c(-c4ccccc4)c4cc5ccccc5cc24)-c2ccc4c5ccc6c7c(-c8ccccc8)c8cccc9c%10ccccc%10c(c89)c7c7ccc(c8ccc-3c2c48)c5c67)cc1] | −15° C. |

As described above, since the organic compound according to the present embodiment has the features (i) to (iii) above, there is provided an organic compound that has a longer emission wavelength of the basic skeleton itself than the comparative compound and that maintains sublimability. Furthermore, when the organic compound according to the present embodiment has the features (iv) and (v) above, there is provided a compound in which intermolecular stacking is suppressed and which can realize improvement in sublimability and suppression of concentration quenching. The use of this organic compound can provide an organic light-emitting element that has high efficiency and high element durability and that exhibits deep red-light emission.

Specific examples of the organic compound according to the present embodiment are shown below. However, the present disclosure is not limited thereto.

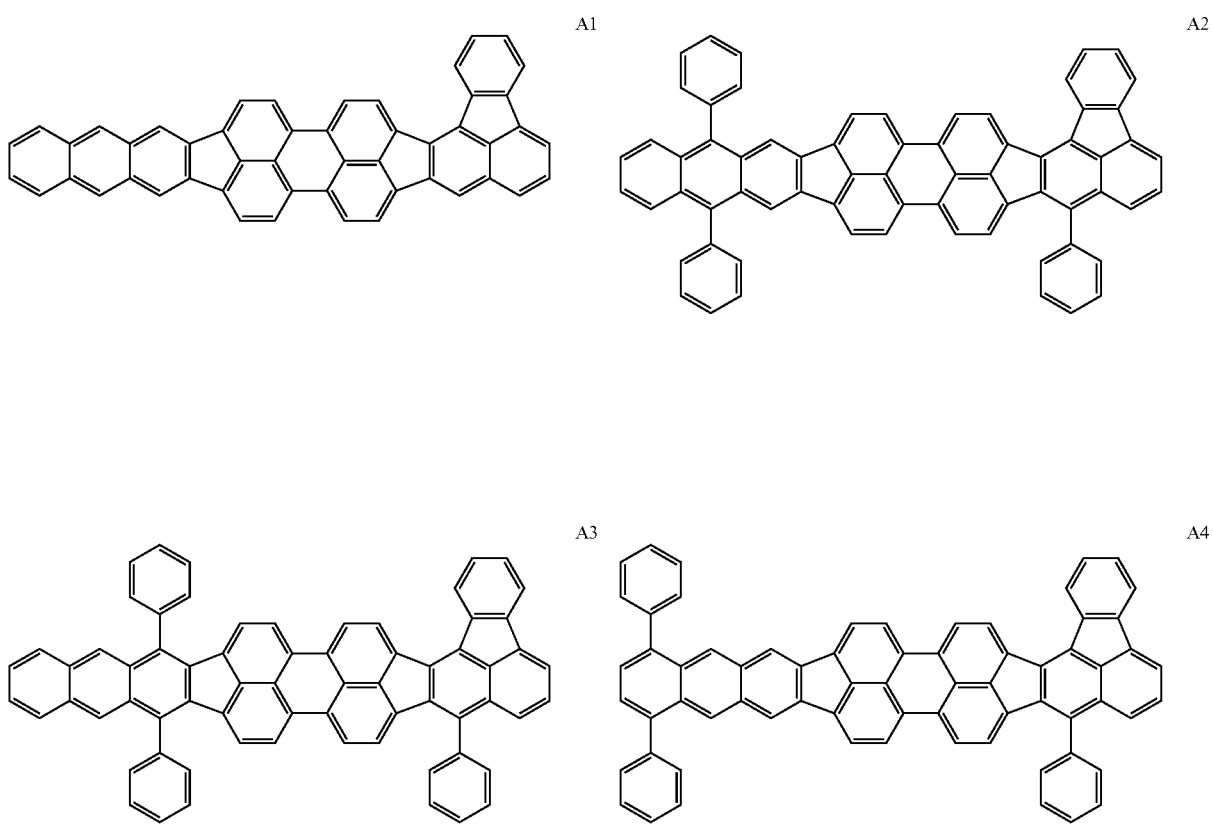

-continued
A5
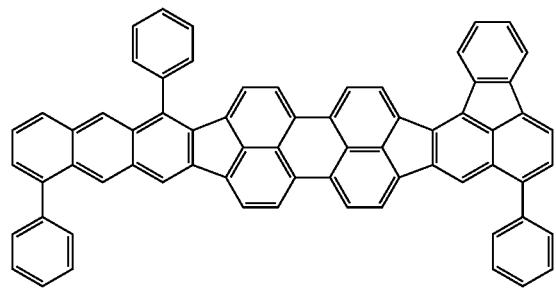
A6
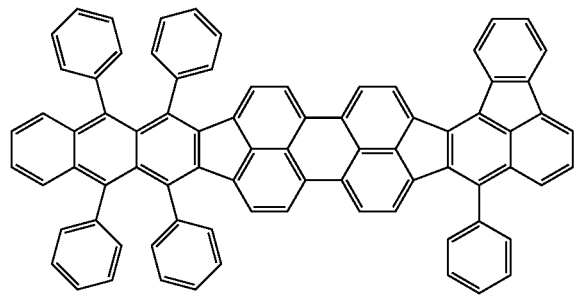
B1
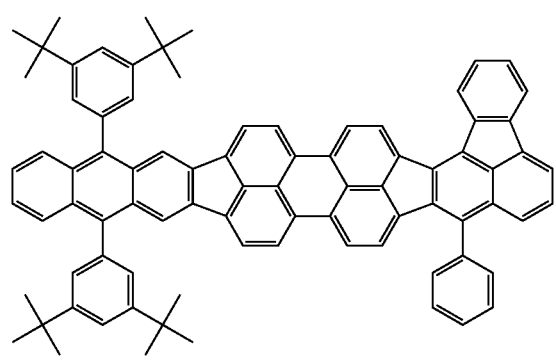
B2
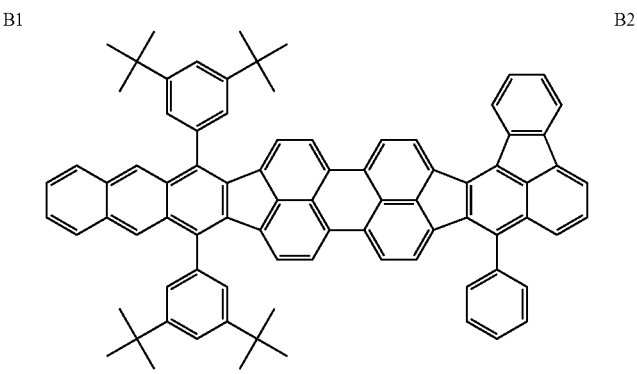
B3
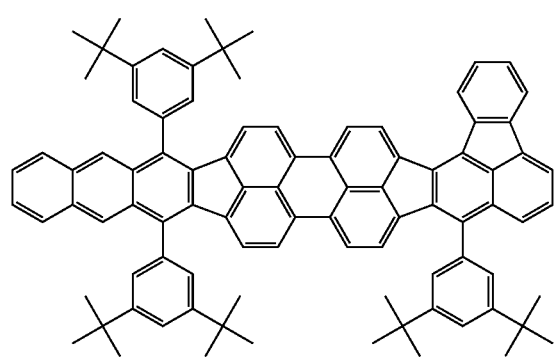
B4
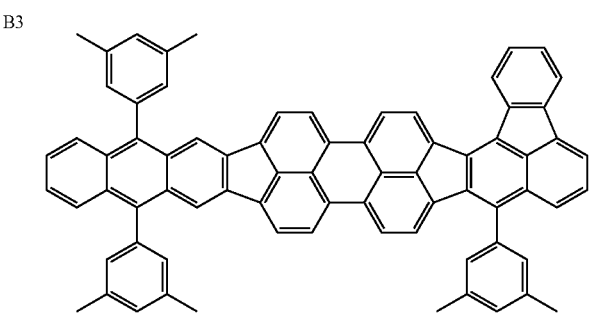
B5
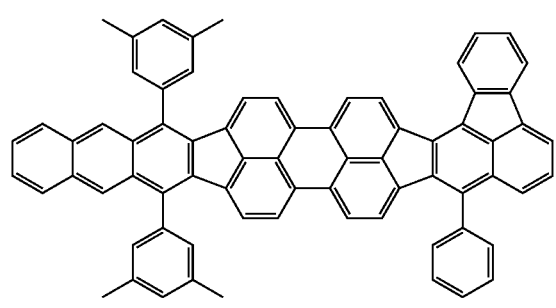
B6
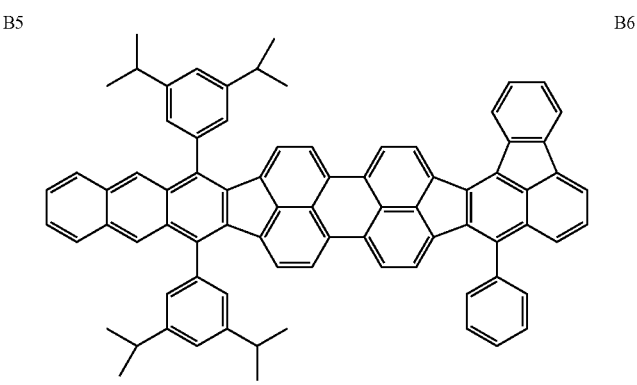

-continued
B7
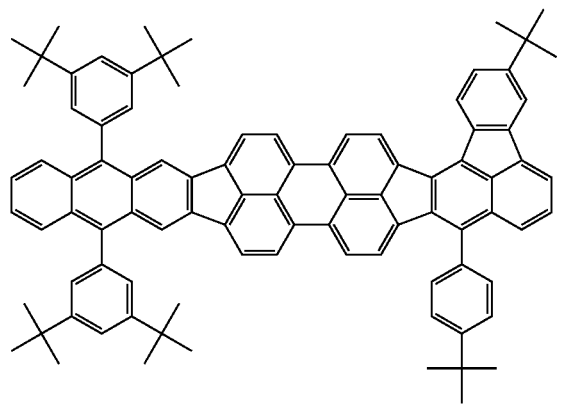
B8
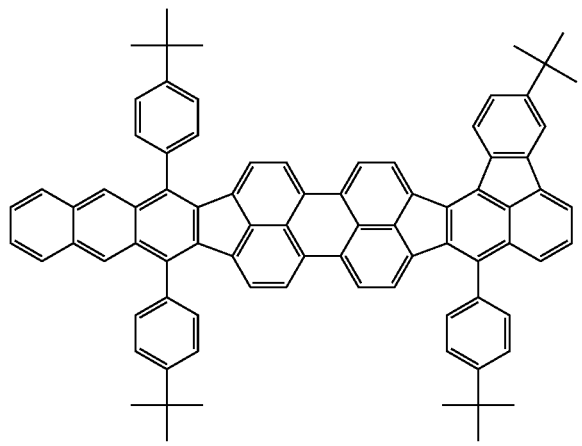
B9
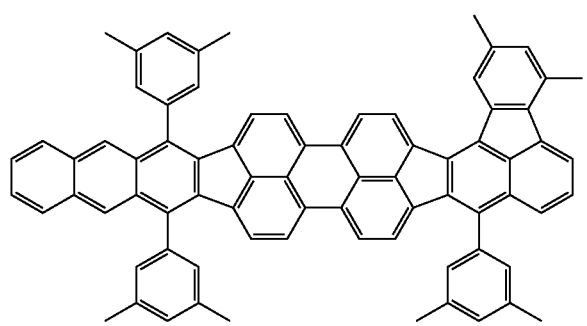
B10
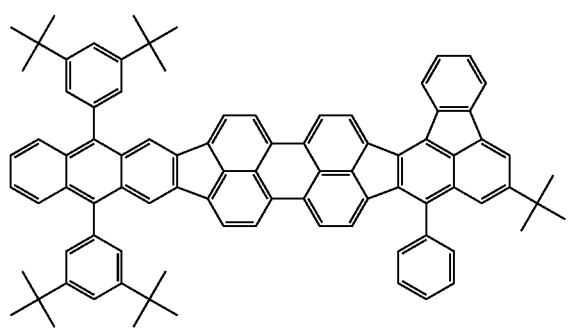
B11
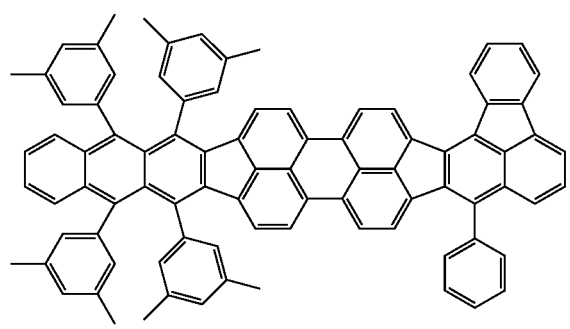
B12
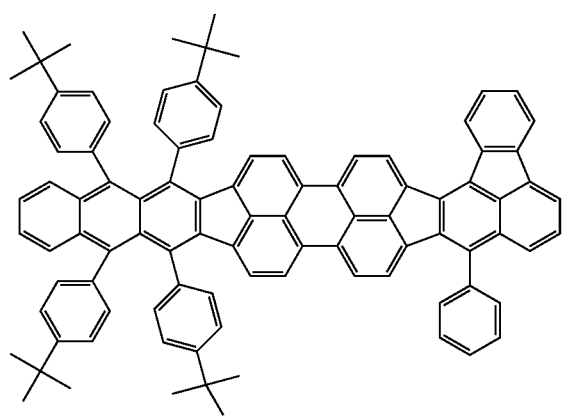
B13
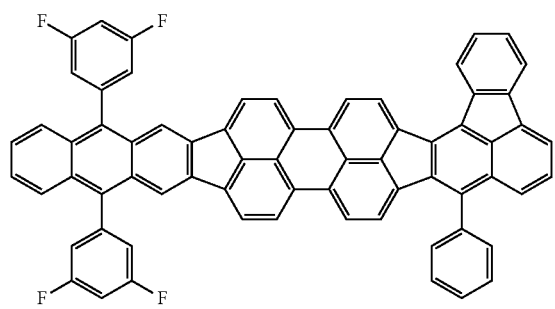
B14
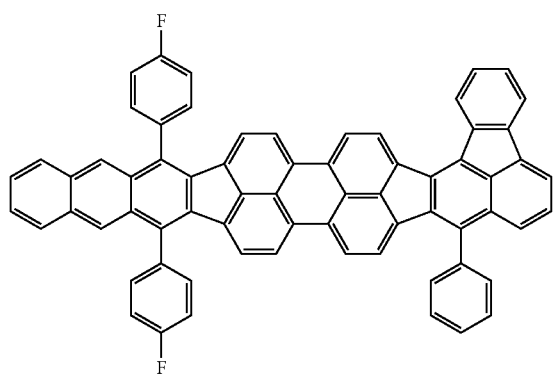

-continued
B15
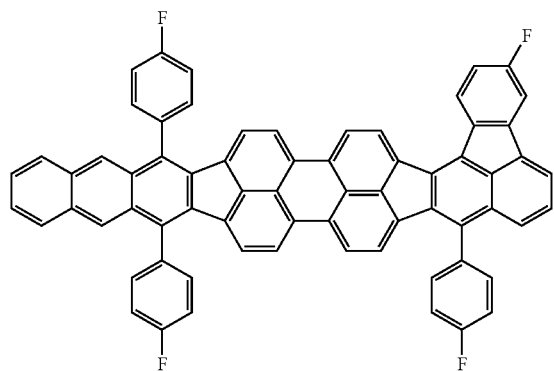
B16
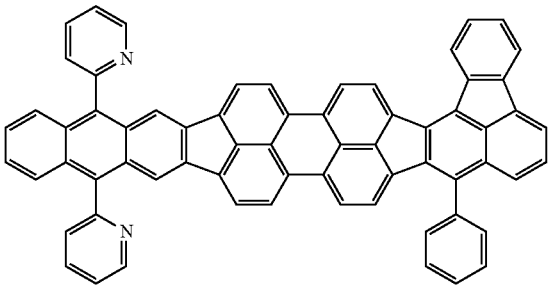
B17
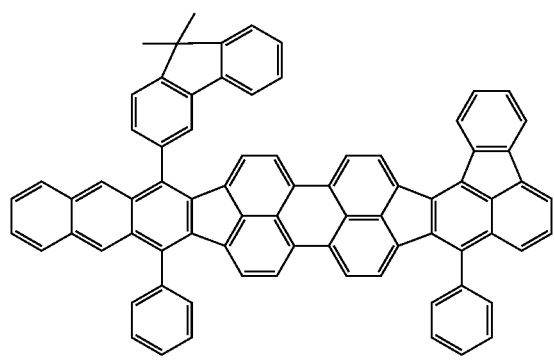
B18
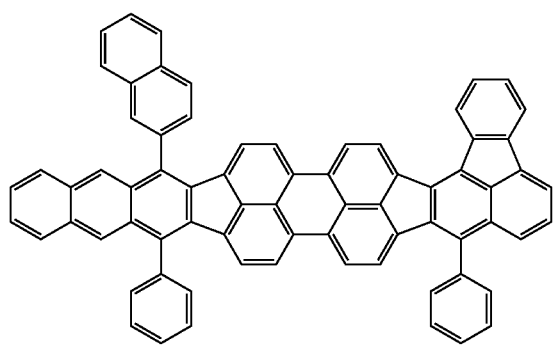
B19
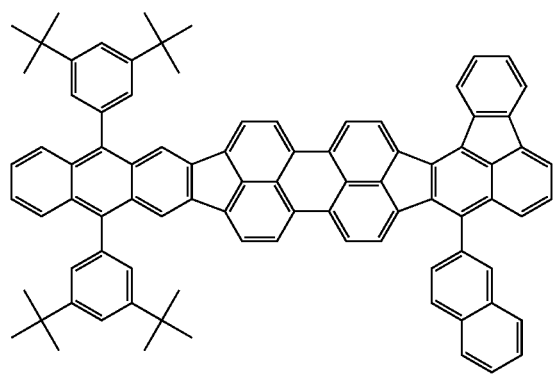
B20
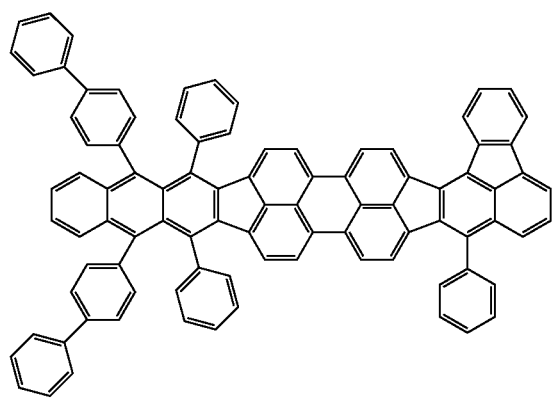
B21
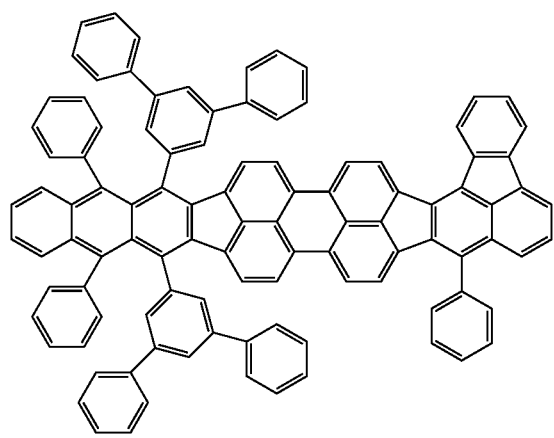
B22
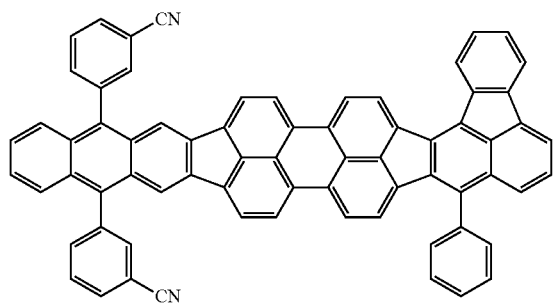

-continued
B23
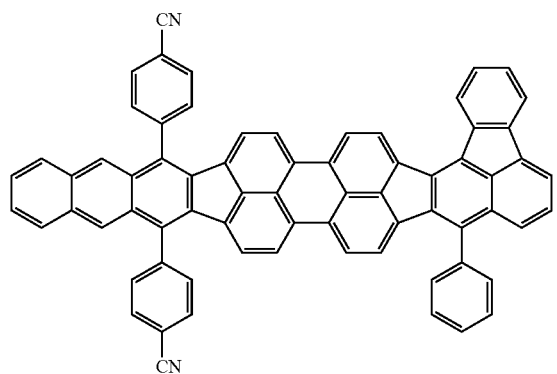
B24
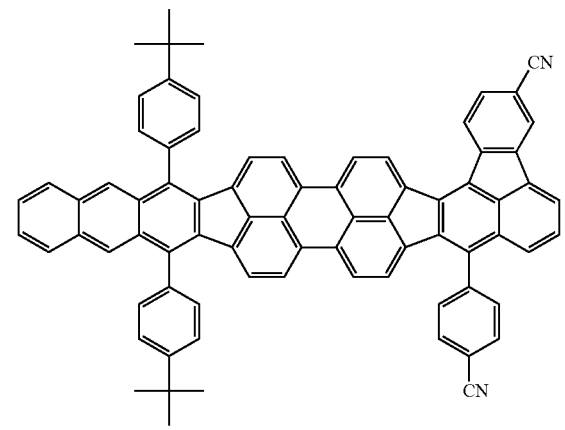
B25
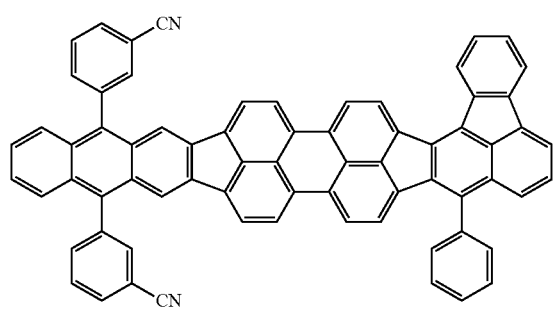
B26
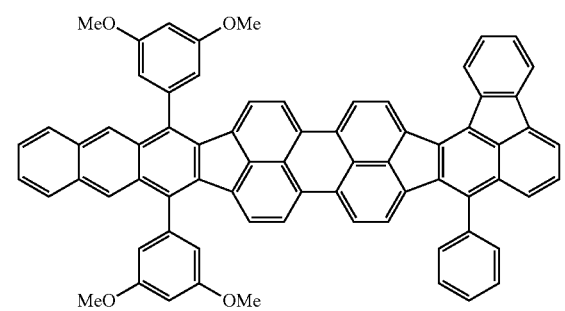
B27
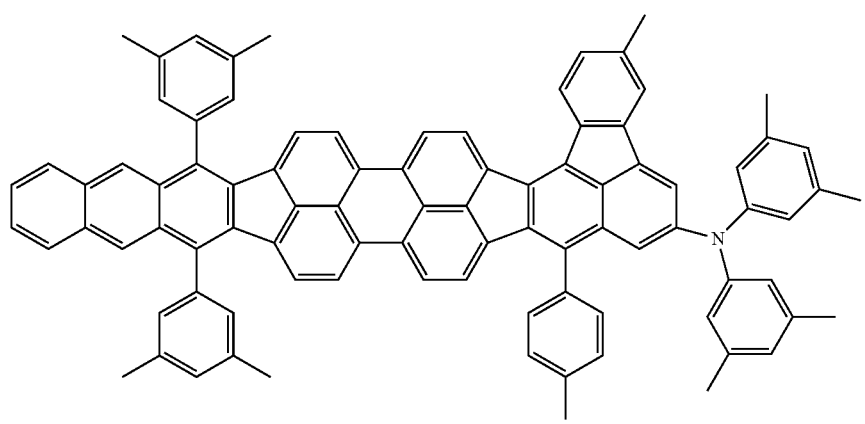
B28
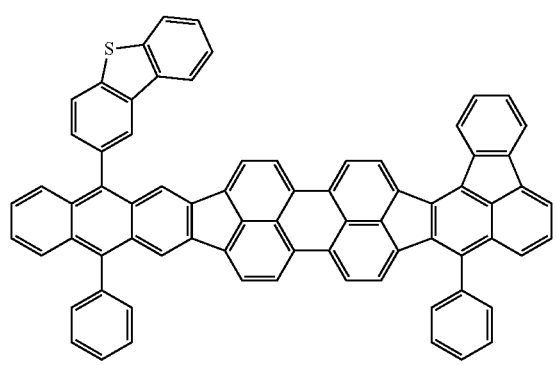
B29
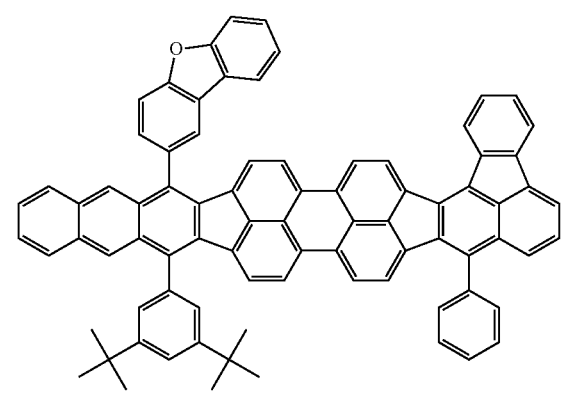

-continued
B30
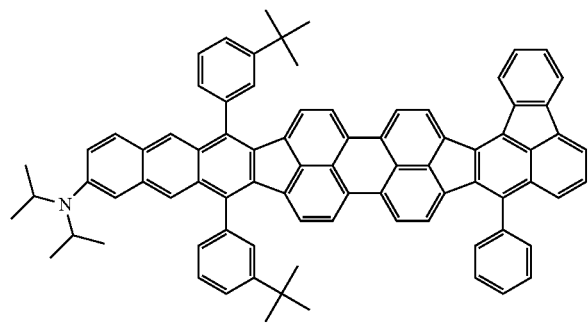
C1
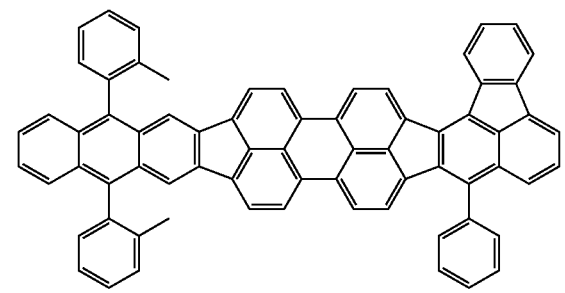
C2
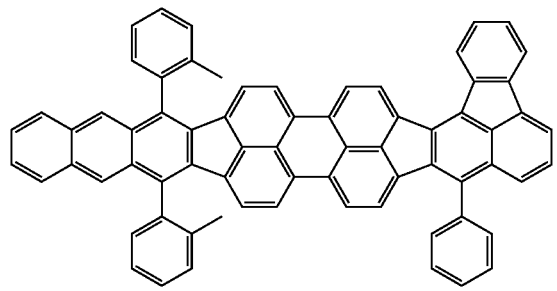
C3
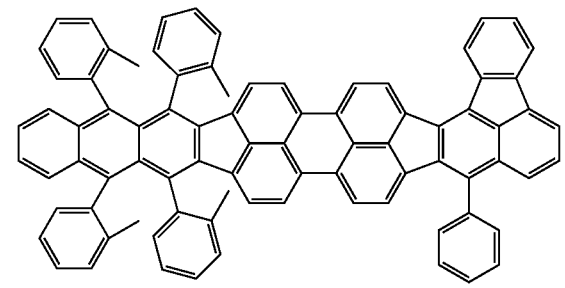
C4
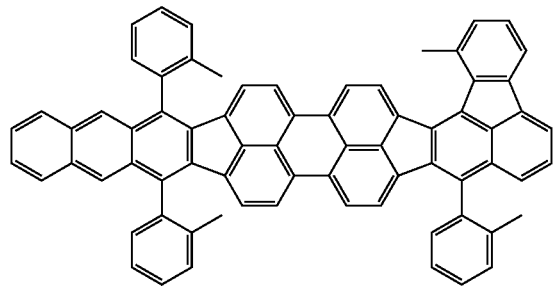
C5
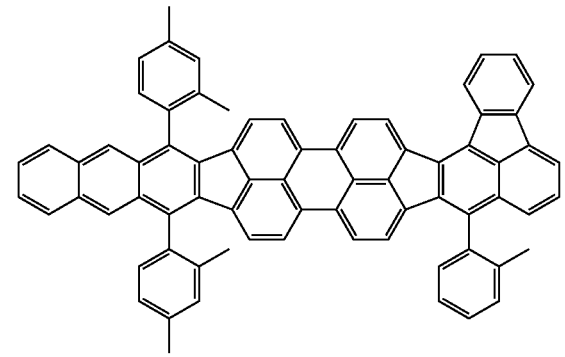
C6
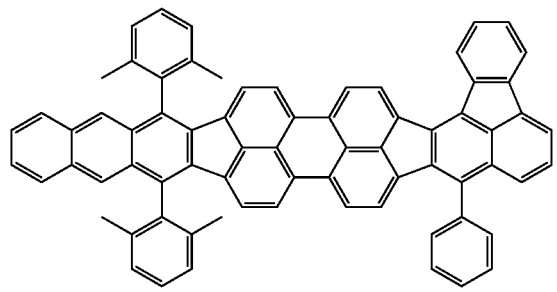
C7
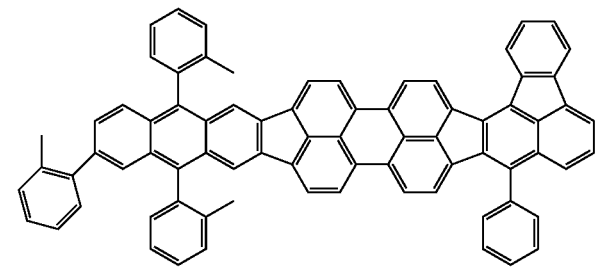

-continued
C8
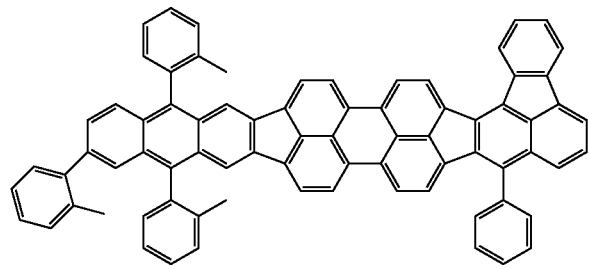
C9
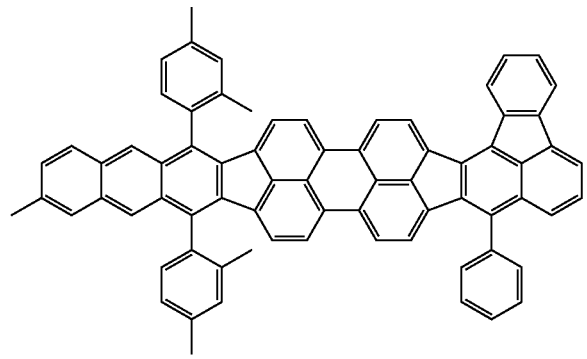
C10
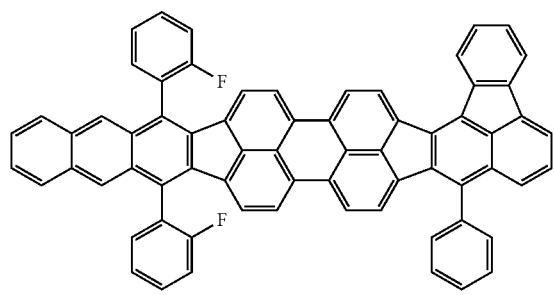
C11
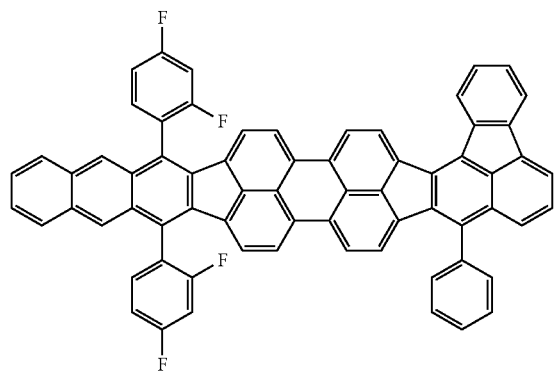
C12
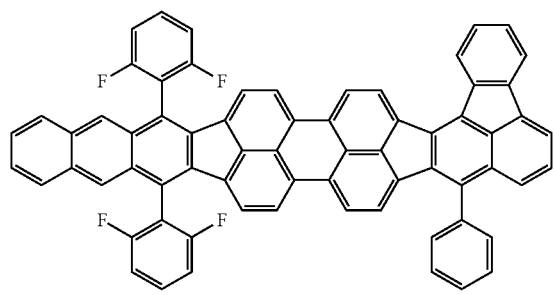
C13
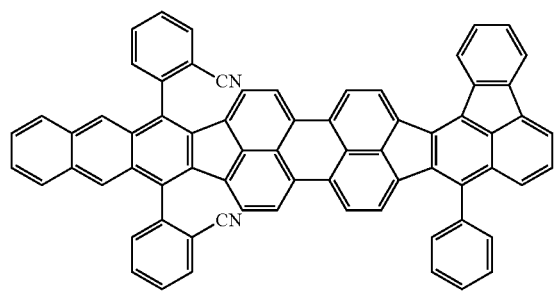
C14
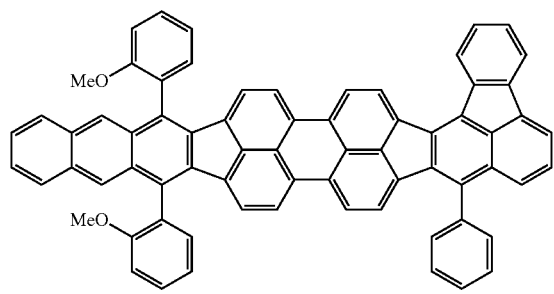
C15
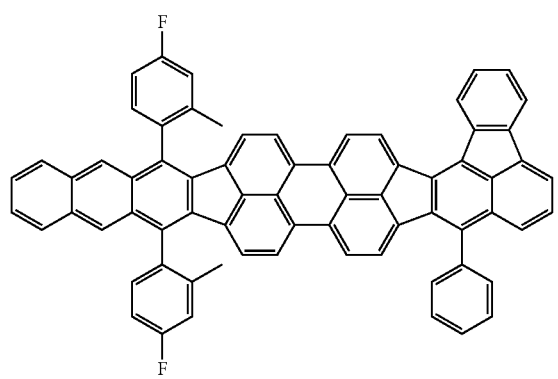

-continued
C16
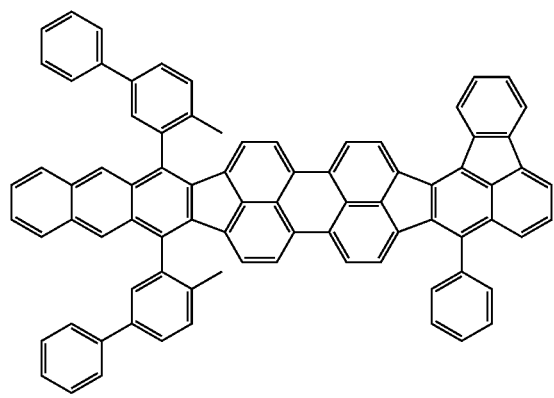
C17
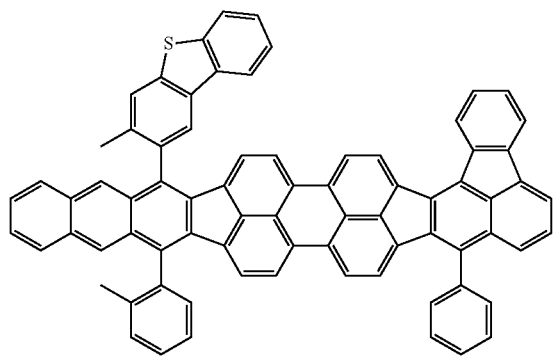
C18
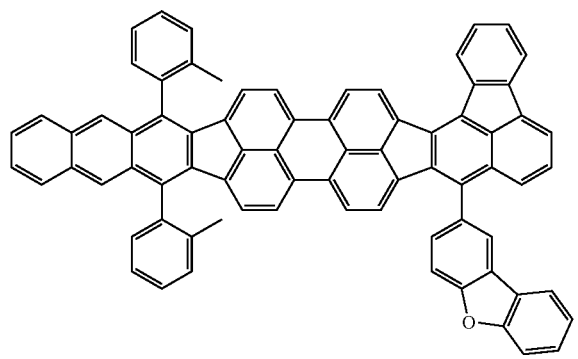
C19
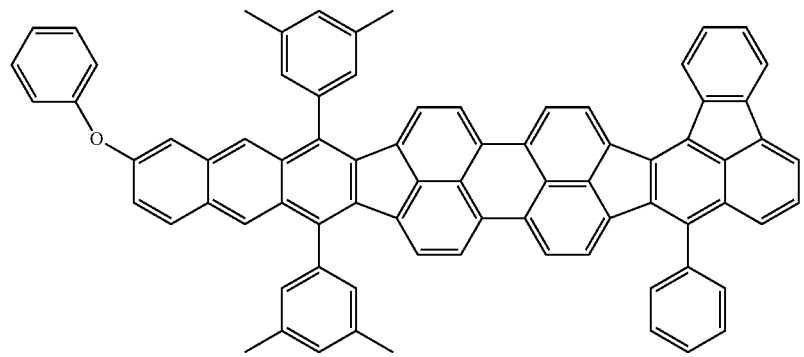
C20
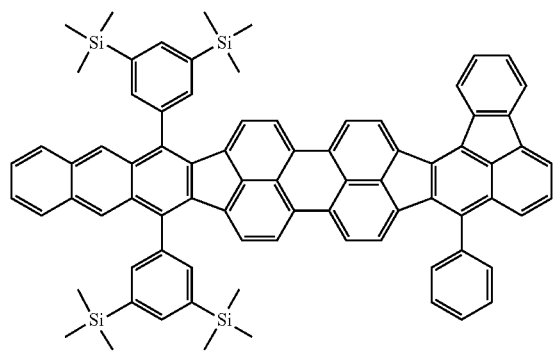
C21
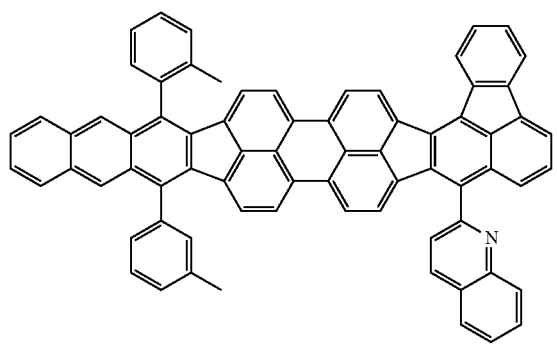

-continued
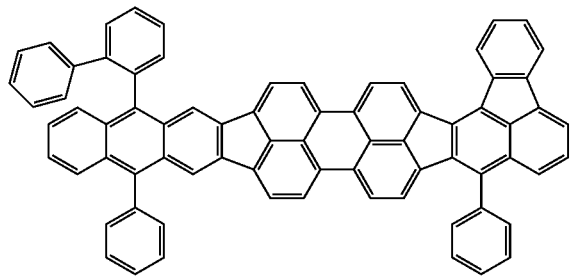

D11 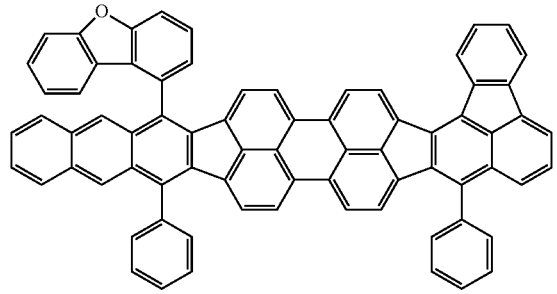

D12 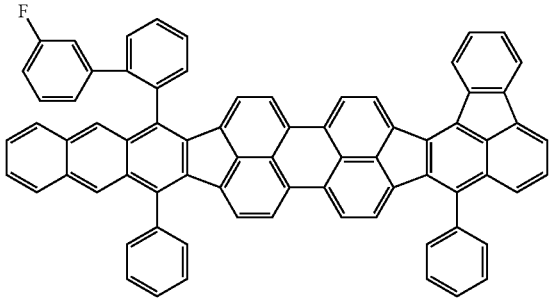

Among the above exemplary compounds, the exemplary compounds belonging to group A are examples in which the whole molecule consists of a hydrocarbon, and the basic skeleton has a phenyl group as a substituent. Here, compounds consisting of hydrocarbons have low HOMO energy levels. Accordingly, the compounds belonging to group A are compounds that have low oxidation potentials, that is, that are stable against oxidation.

Accordingly, among the compounds according to the present embodiment, organic compounds consisting of hydrocarbons, that is, the compounds belonging to group A are preferred because of their high molecular stability. The compounds belonging to group A can be used as a light-emitting-layer host material, a transport layer, or an injection layer.

Among the above exemplary compounds, the exemplary compounds belonging to group B have a basic skeleton that has, as a substituent, an aryl group having a substituent, a polycyclic aryl group, an aryl group having a heteroatom, or an amino group. The substituent contained in the aryl group may be an alkyl group, a halogen atom such as a fluorine atom, a cyano group, or an alkoxy group. In the compounds having an alkyl group or fluorine, intermolecular stacking is suppressed. When such compounds are used as a light-emitting-layer guest material, concentration quenching can be suppressed. In addition, the exemplary compounds belonging to group B are compounds having high sublimability because a sublimation or vapor deposition start temperature decreases to increase the difference between this temperature and the decomposition temperature. Furthermore, since the solubility of the compounds improve, the compounds can be used as materials for coating.

Compounds having an alkoxy group or an aryloxy group, or a silyl group similarly have the effect of suppressing concentration quenching and can be used as materials for coating. In compounds having a nitrogen-containing heterocyclic group or a cyano group, an effect of withdrawing an electron acts with respect to the basic skeleton. Thus, these compounds have a lower HOMO energy level and are more stable against oxidation than the compounds belonging to group A. In compounds having an amino group, an effect of donating an electron acts with respect to the basic skeleton. Thus, these compounds have a narrow bandgap and emit light having a longer wavelength. Compounds having an aryl group having 7 or more carbon atoms or a heterocyclic group have a higher glass transition temperature than compounds substituted with a phenyl group. Accordingly, when these compounds are used as a light-emitting-layer host material or a transport layer, a thermally stable amorphous film is formed.

Among the above exemplary compounds, the exemplary compounds belonging to group C are examples in which the basic skeleton is substituted with a phenyl group, and the phenyl group has a substituent at an ortho position thereof. The substituent may be an alkyl group, a halogen atom such as a fluorine atom, an alkoxy group, and a cyano group. Since the phenyl group has a substituent at an ortho position thereof, the phenyl group is twisted with respect to the basic skeleton, and the substituent at the ortho position covers the π-conjugated plane of the basic skeleton to suppress molecular stacking. Since the exemplary compounds belonging to group C have a substituent at an ortho position of a phenyl group, the exemplary compounds belonging to group C are compounds in which intermolecular stacking is suppressed and which have high sublimability compared with the exemplary compounds belonging to group B. In addition, the use of the exemplary compounds belonging to group C as a light-emitting-layer guest material enables concentration quenching to be suppressed.

Among the above exemplary compounds, the exemplary compounds belonging to group D are examples in which the basic skeleton is substituted with a phenyl group, and the phenyl group further has a phenyl group at an ortho position thereof. Since the effect of covering the π-conjugated plane of the basic skeleton is higher than that in group C, molecular stacking is further suppressed. Therefore, the exemplary compounds belonging to group D are compounds in which intermolecular stacking is suppressed and which have high sublimability compared with the exemplary compounds belonging to group C.

Next, an organic light-emitting element of the present embodiment will be described.

An organic light-emitting element of the present embodiment at least includes an anode and a cathode, which are a pair of electrodes, and an organic compound layer disposed between the electrodes. In the organic light-emitting element of the present embodiment, the organic compound layer may be formed of a single layer or a layered product including a plurality of layers as long as the organic compound layer includes a light-emitting layer.

When the organic compound layer is a layered product including a plurality of layers, the organic compound layer may include, besides a light-emitting layer, for example, a hole injection layer, a hole transport layer, an electron blocking layer, a charge generation layer, a hole/exciton blocking layer, an electron transport layer, and an electron injection layer. The light-emitting layer may be a single layer or a layered product including a plurality of layers.

In the organic light-emitting element of the present embodiment, at least one layer included in the organic compound layer contains the organic compound according to the present embodiment. Specifically, the organic compound according to the present embodiment is contained in any of the hole injection layer, the hole transport layer, the electron blocking layer, the light-emitting layer, the hole/exciton blocking layer, the electron transport layer, and the electron injection layer. The organic compound according to the present embodiment is preferably contained in the light-emitting layer.

When the organic compound according to the present embodiment is contained in a light-emitting layer in the organic light-emitting element of the present embodiment, the light-emitting layer may be a layer consisting of the organic compound according to the present embodiment or a layer that contains the organic compound according to the present embodiment and another compound. When the light-emitting layer is a layer containing the organic compound according to the present embodiment and another compound, the organic compound according to the present embodiment may be used as a host of the light-emitting layer or a guest of the light-emitting layer. Alternatively, the organic compound according to the present embodiment may be used as an assist material that can be contained in the light-emitting layer.

Herein, the host refers to, among the compounds that form the light-emitting layer, a compound having the highest weight ratio. The guest refers to, among the compounds that form the light-emitting layer, a compound that has a lower weight ratio than the host and that is responsible for main light emission. The assist material refers to, among the compounds that form the light-emitting layer, a compound that has a lower weight ratio than the host and that assists light emission of the guest. The assist material is also referred to as a second host. When the composition of the light-emitting layer of the organic light-emitting element is assumed to be uniform, the composition of the entire light-emitting layer can be determined by analyzing a portion of the light-emitting layer.

When the organic compound according to the present embodiment is used as the guest of the light-emitting layer, the concentration of the guest is preferably 0.01% by weight or more and 20% by weight or less and more preferably 0.1% by weight or more and 5% by weight or less of the total of the light-emitting layer.

When the organic compound according to the present embodiment is used as the guest of the light-emitting layer, a material having a higher LUMO energy level than the organic compound according to the present embodiment (a material having a LUMO energy level closer to the vacuum level) may be used as the host. This is because the organic compound according to the present embodiment has a low LUMO energy level, and thus the use of a compound having a higher LUMO energy level than the organic compound of the present embodiment as the host enables the organic compound according to the present embodiment to receive a larger part of the electrons supplied to the host of the light-emitting layer.

As a results of various studies, the inventors of the present inventors have found that the use of the organic compound according to the present embodiment as the host or the guest, in particular, as the guest of a light-emitting layer provides an element that produces optical output with high efficiently and high luminance and that has extremely high durability. This light-emitting layer may be formed of a single layer or may have a multilayer structure. The light-emitting layer may contain another luminescent material having another emission color so as to emit a color light mixed with red which is the emission color of the present embodiment. The multilayer structure refers to a state where the light-emitting layer and another light-emitting layer are stacked. In such a case, the emission color of the organic light-emitting element is not limited to red. More specifically, the emission color may be white or intermediate color. When the emission color is white, the other light-emitting layer emits light of a color other than red, such as blue or green. The light-emitting layer is formed by a method such as vapor deposition or coating. Details of the method will be more specifically described in Examples below.

The organic compound according to the present embodiment can be used as a material that forms an organic compound layer other than the light-emitting layer included in an organic light-emitting element of the present embodiment. Specifically, the organic compound according to the present embodiment may be used as a material that forms an electron transport layer, an electron injection layer, a hole transport layer, a hole injection layer, a hole blocking layer, or the like. In such a case, the emission color of the organic light-emitting element is not limited to red. More specifically, the emission color may be white or intermediate color.

Herein, the organic compound according to the present embodiment may be used in combination with a known low-molecular-weight or high-molecular-weight hole injection compound or hole transport compound, a compound serving as the host, a luminous compound, an electron injection compound, an electron transport compound, and the like, as required.

Examples of these compounds will be described below. A hole injection or transport material is preferably a material having a high hole mobility so as to facilitate hole injection from the anode and to enable the injected holes to be transported to the light-emitting layer. From the viewpoint of suppressing deterioration of the film quality such as crystallization in the organic light-emitting element, a material having a high glass transition temperature is preferred. Examples of the low-molecular-weight or high-molecular-weight material having a hole injection or transport performance include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used as an electron blocking layer.

Specific examples of the compound used as the hole injection or transport material are shown below but are not limited thereto.

HT1
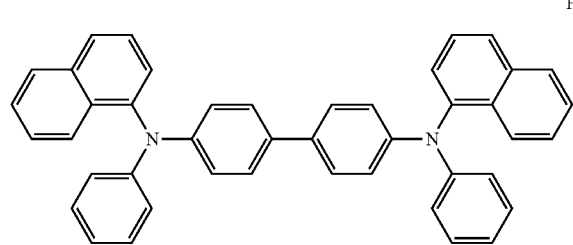
HT2
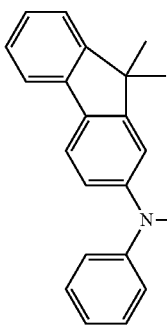
HT3
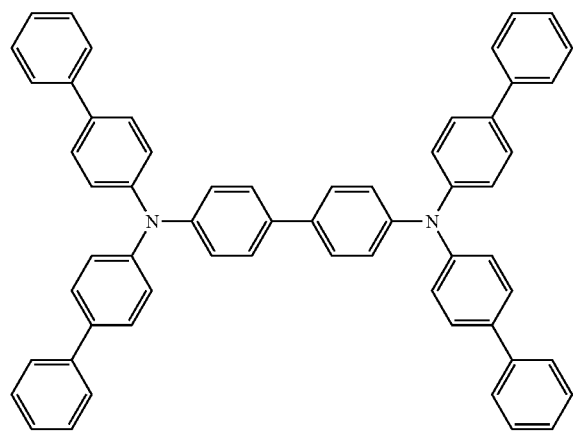
HT4
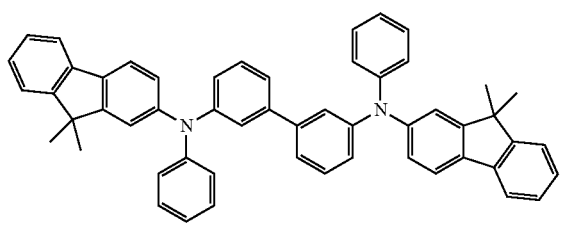
HT5
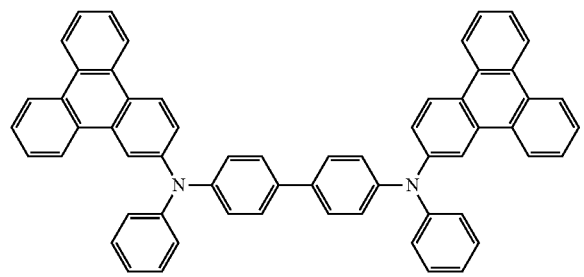
HT6
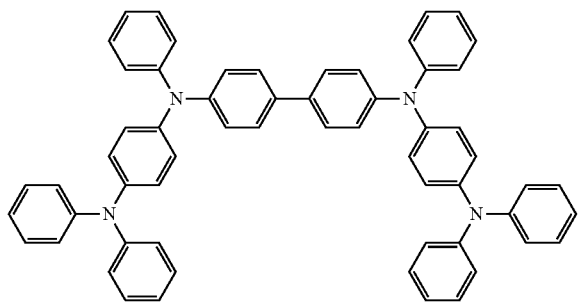
HT7
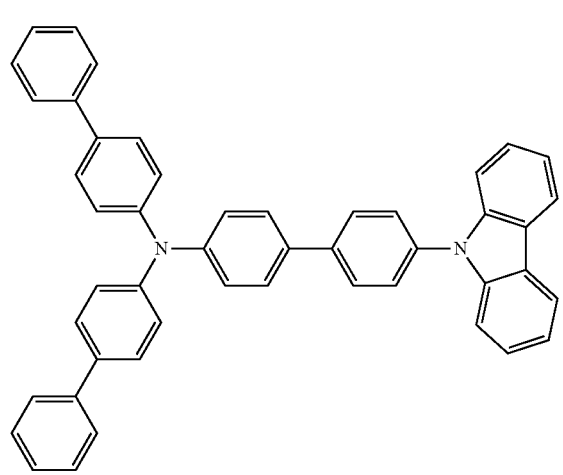
HT8
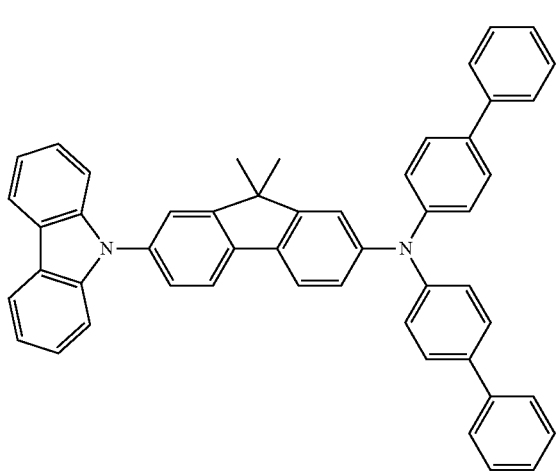

-continued
HT-9
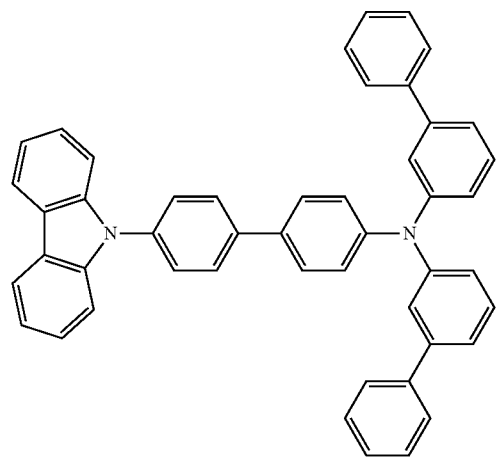
HT-10
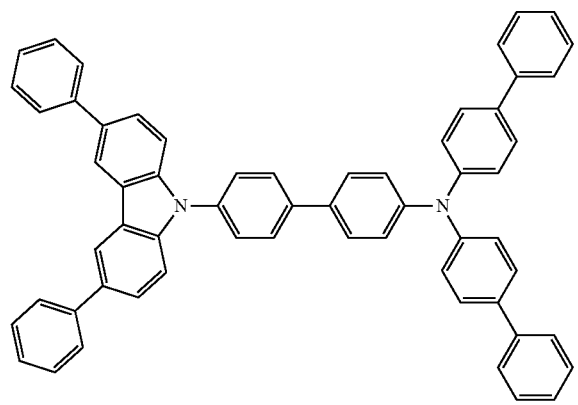
HT-11
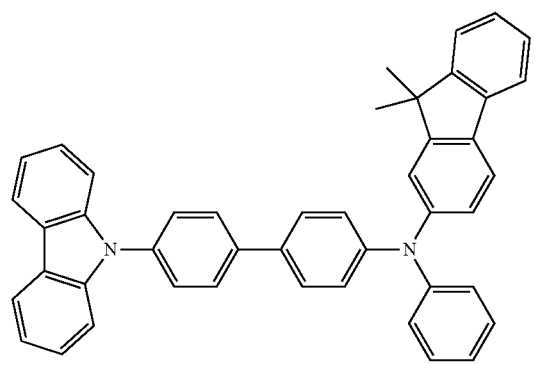
HT-12
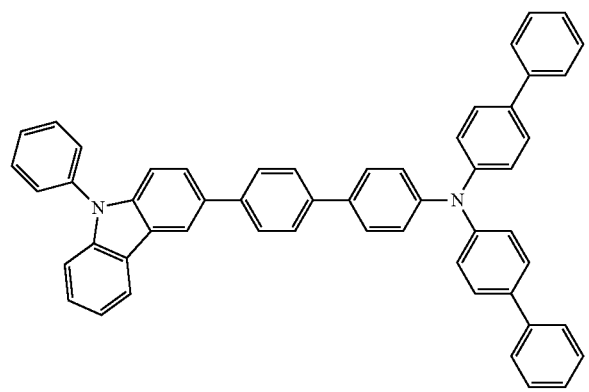
HT-13
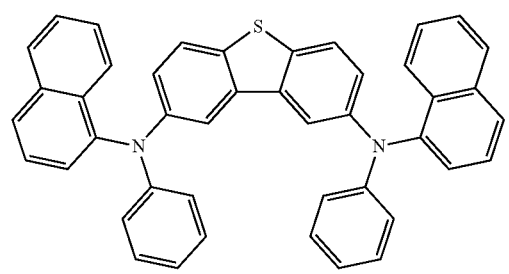
HT-14
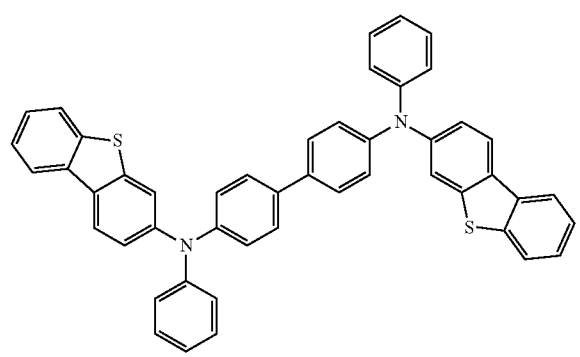

-continued

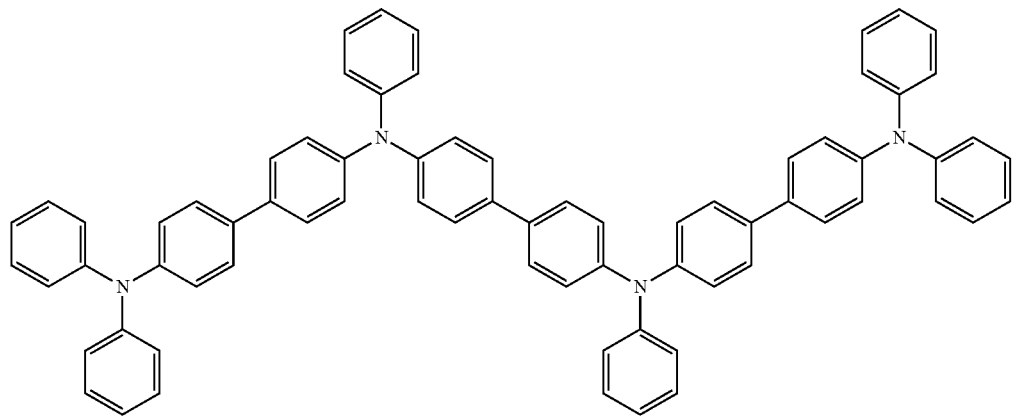
HT-15

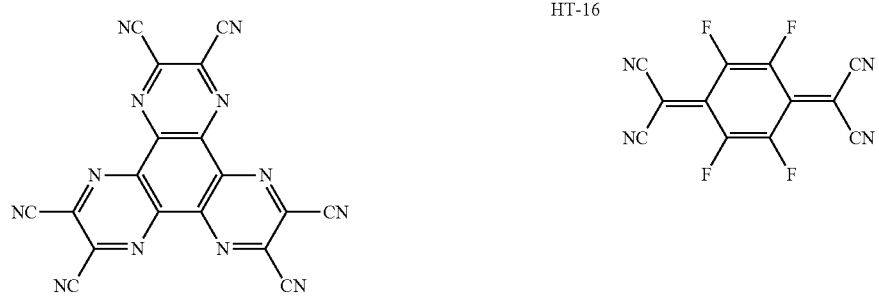
HT-16  HT-17

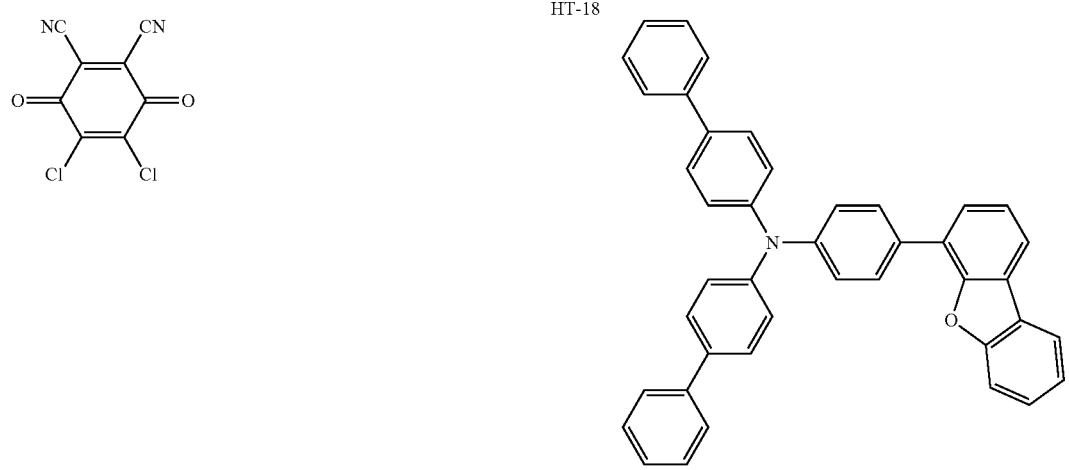
HT-18  HT-19

Examples of the luminescent material that mainly relates to the function of light emission include, besides the organic compound represented by general formula (1), fused ring compounds (such as fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

The organic compound according to the present embodiment is a compound having a narrow bandgap and a low HOMO/LUMO energy level. Accordingly, when a mixture layer is formed with another luminescent material or light-emitting layers are stacked, similarly, the other luminescent material also preferably has a low HOMO/LUMO energy level. This is because when the other luminescent material has a high HOMO/LUMO energy level, a quenching component or a trap level may be formed, for example, the other luminescent material may form an exciplex together with the organic compound according to the present embodiment.

Specific examples of the compound used as the luminescent material are shown below but are not limited thereto.

-continued

BD1

BD2

BD3

BD4

BD5

BD6

BD7

BD8

GD1

GD2
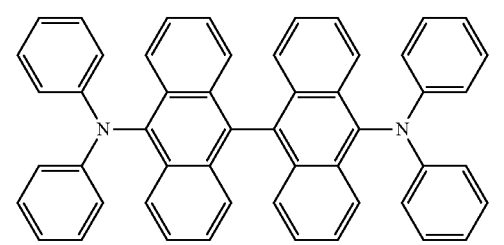
GD3
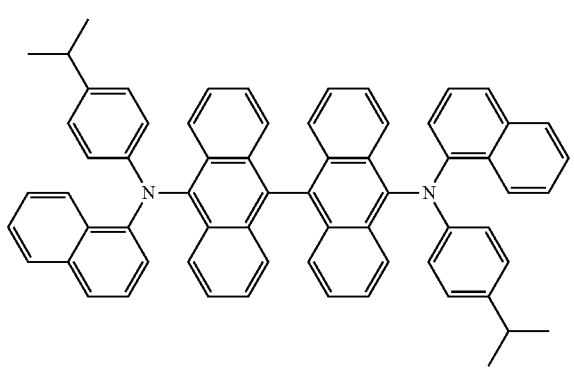
GD4
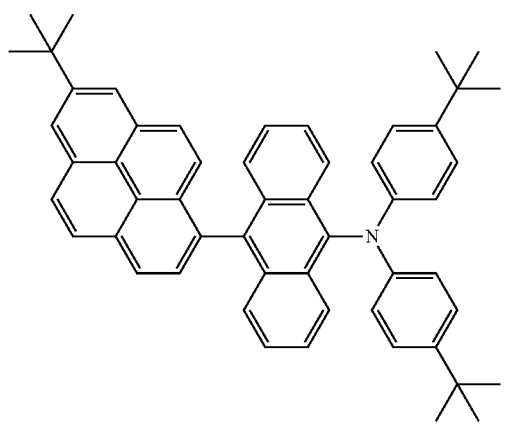
GD5
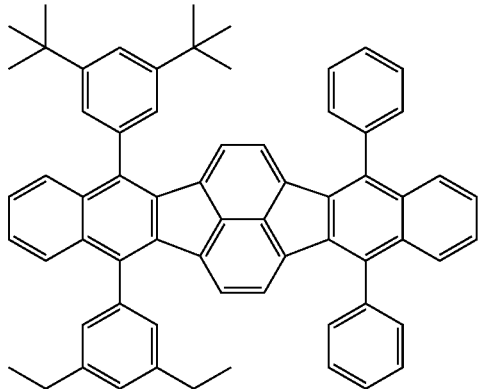
GD6
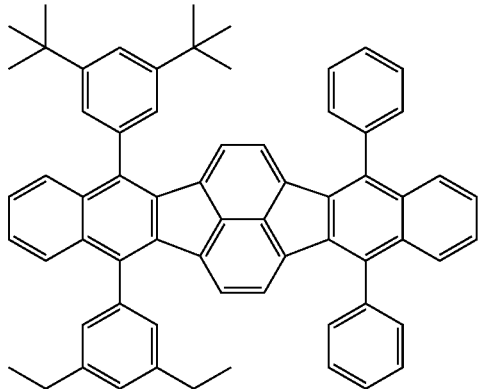
GD7
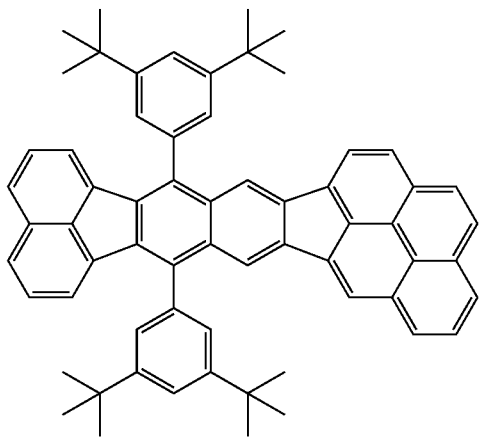
GD8
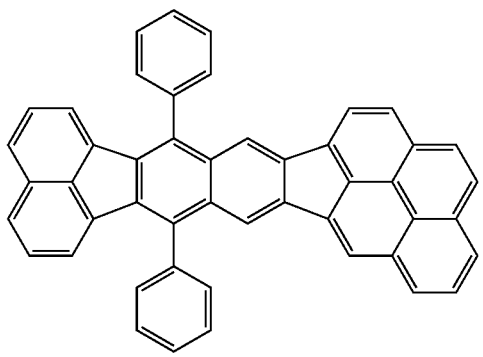

GD9

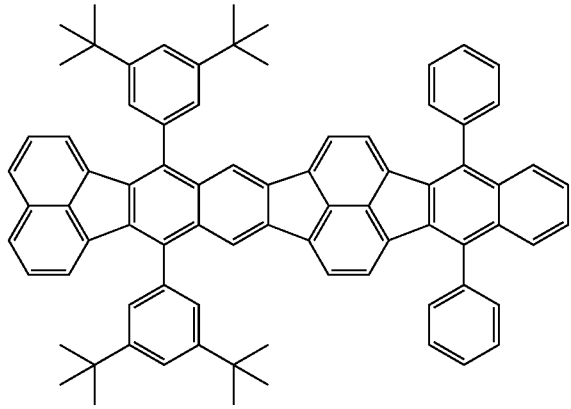

GD10

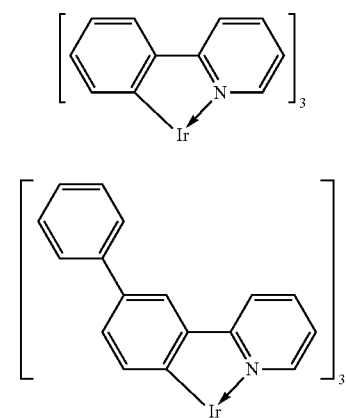

GD11

GD12

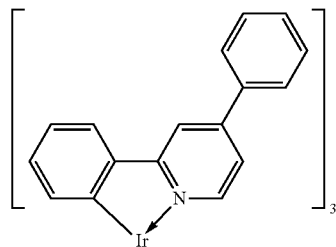

Examples of the light-emitting-layer host or the light-emission assist material that is contained in the light-emitting layer include, besides aromatic hydrocarbon compounds and derivatives thereof, carbazole derivatives, dibenzofuran derivatives, dibenzothiophene derivatives, organoaluminum complexes such as tris(8-quinolinolato) aluminum, and organoberyllium complexes.

The organic compound according to the present embodiment is a compound having a narrow bandgap and a low HOMO/LUMO energy level. Accordingly, preferably, the host material is also formed of a hydrocarbon and similarly has a low HOMO/LUMO energy level. This is because when the host material contains a heteroatom such as a nitrogen atom, the HOMO/LUMO energy level becomes high, and a quenching component or a trap level may be formed, for example, the host material may form an exciplex together with the organic compound of the present embodiment.

The host material particularly preferably has an anthracene, tetracene, perylene, or pyrene skeleton in its molecular skeleton. This is because such a compound is constituted by a hydrocarbon as described above and has Si energy capable of causing the organic compound of the present embodiment to sufficient energy transfer.

Specific examples of the compound used as the light-emitting-layer host or light-emission assist material that is contained in the light-emitting layer are shown below but are not limited thereto.

EM1

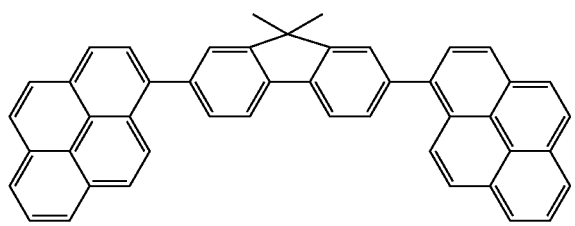

EM2

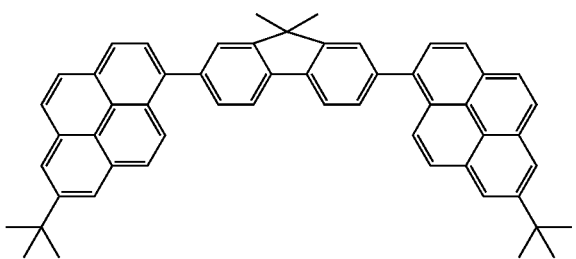

EM3

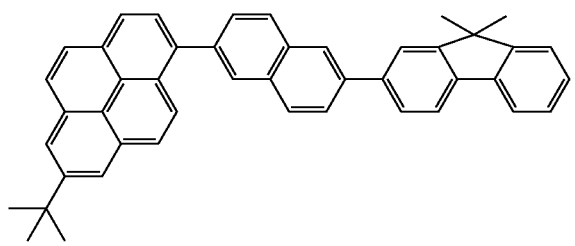

EM4

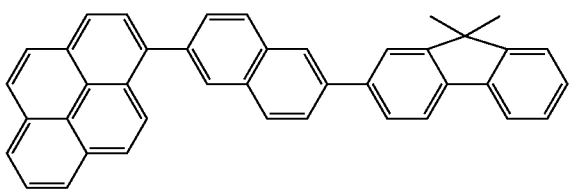

-continued
EM5
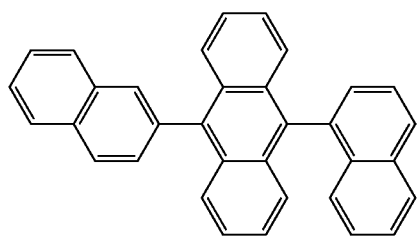
EM6
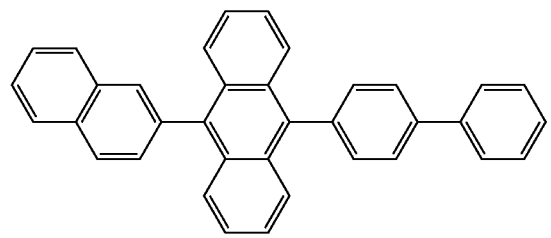
EM7
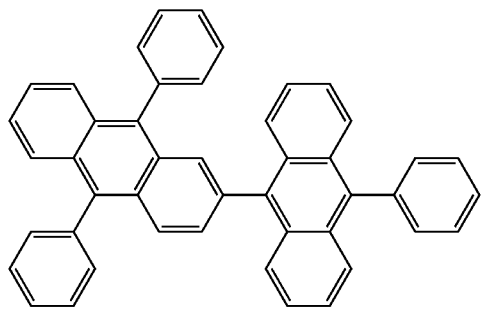
EM8
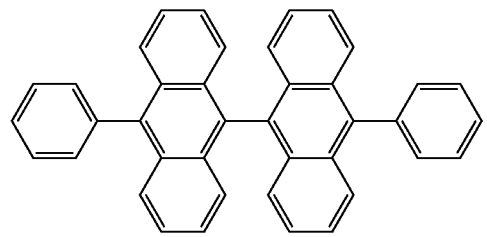
EM9
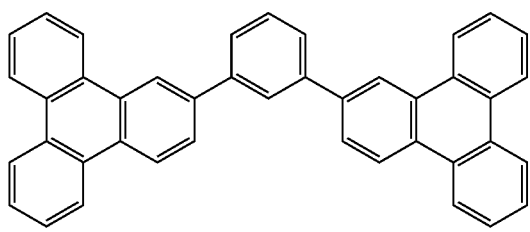
EM10
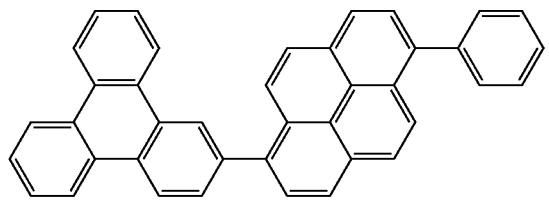
EM11
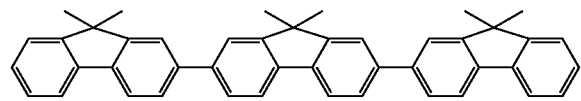
EM12
EM13
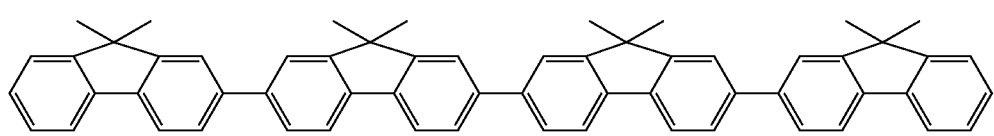
EM14
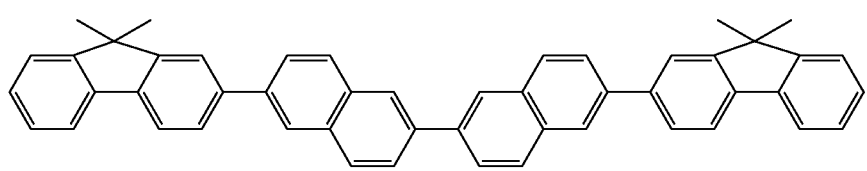

-continued
EM15
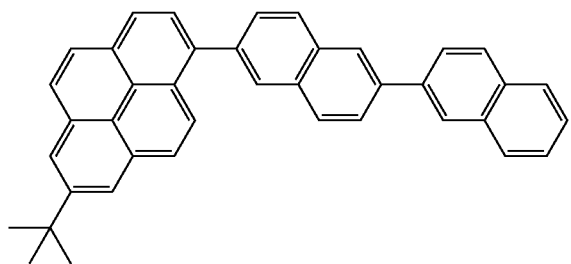
EM16
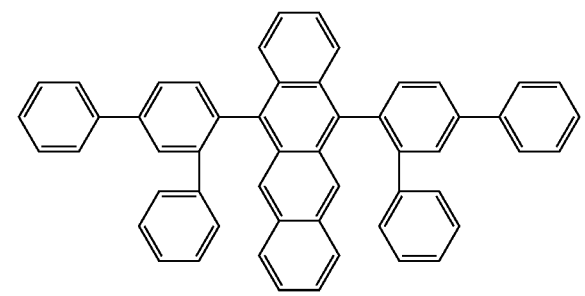
EM17
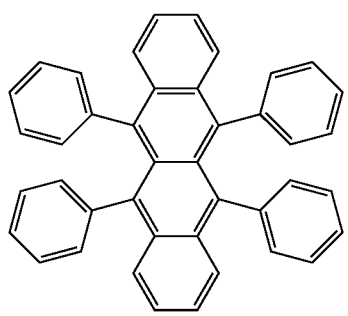
EM18
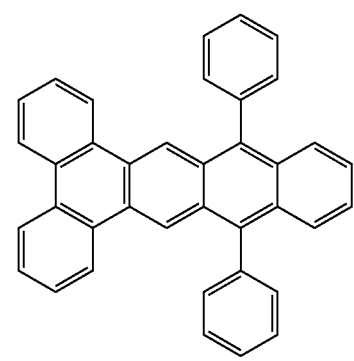
EM19
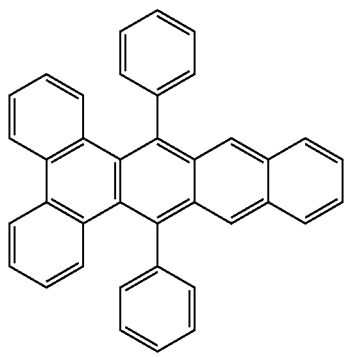
EM20
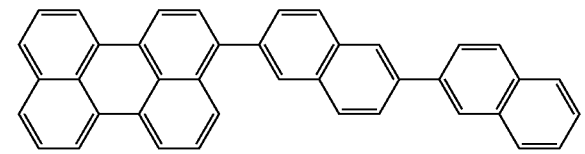
EM21
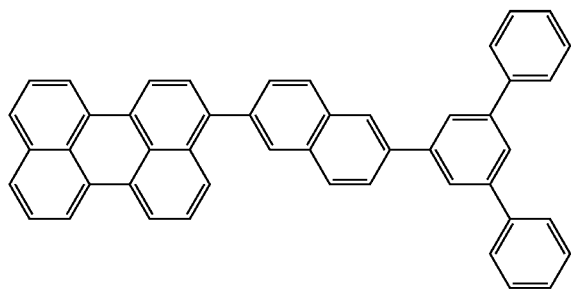
EM22
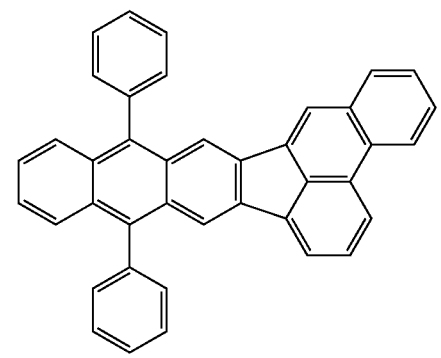

-continued
EM23
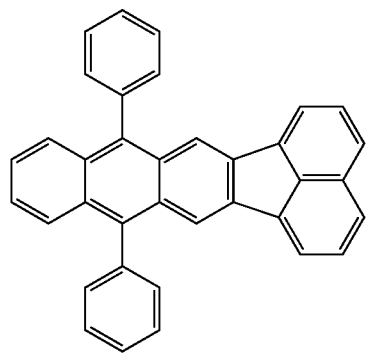
EM24
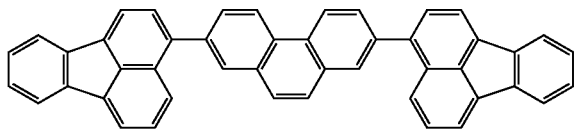
EM25
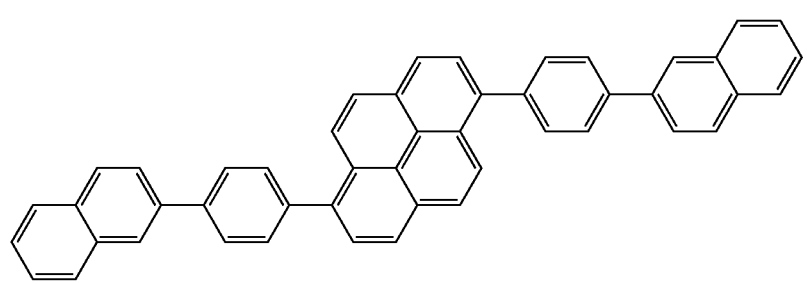
EM26
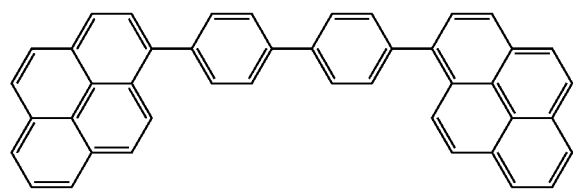
EM27
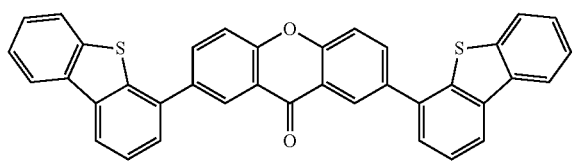
EM28
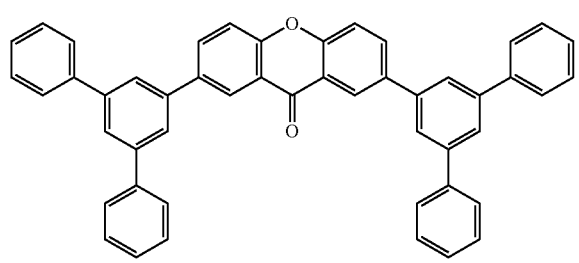
EM29
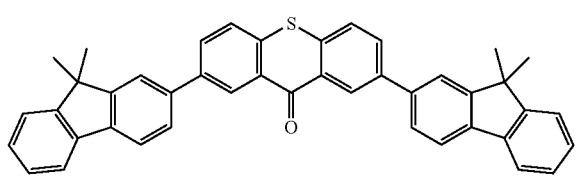
EM30
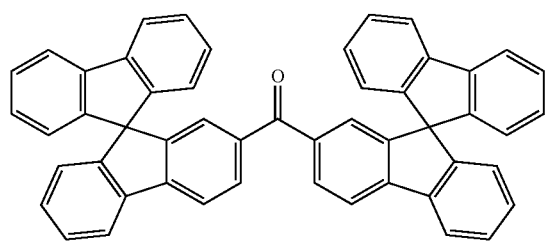
EM31
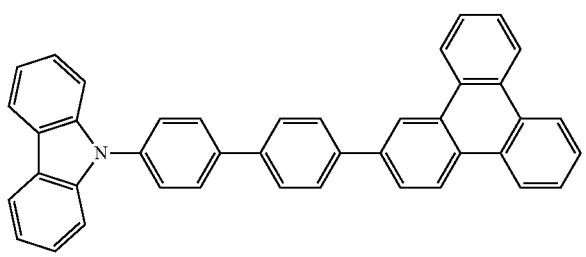

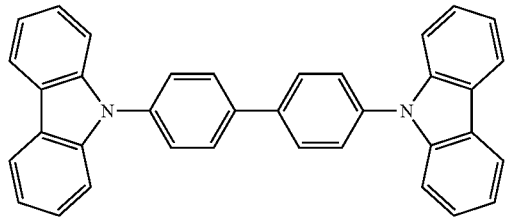

EM32

The electron transport material can be freely selected from materials capable of transporting electrons injected from the cathode to the light-emitting layer and is selected in consideration of, for example, the balance with the hole mobility of the hole transport material. Examples of the material having an electron transport performance include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (such as fluorene derivatives, naphthalene derivatives, chrysene derivatives, and anthracene derivatives). The above electron transport material is also suitably used as a hole blocking layer.

Specific examples of the compound used as the electron transport material are shown below but are not limited thereto.

ET1

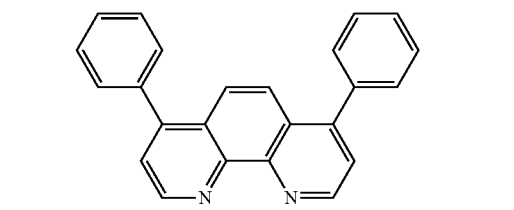

ET2

ET3

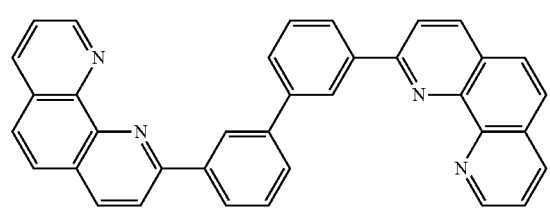

ET4

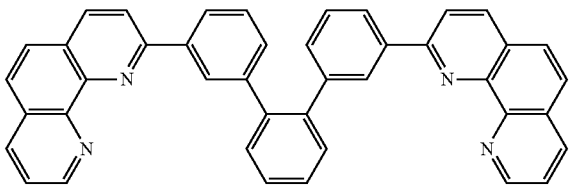

ET5

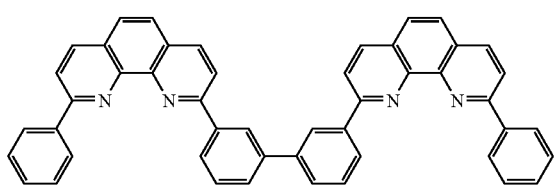

ET6

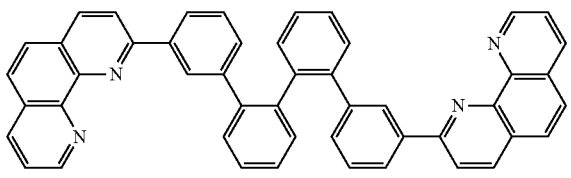

ET7

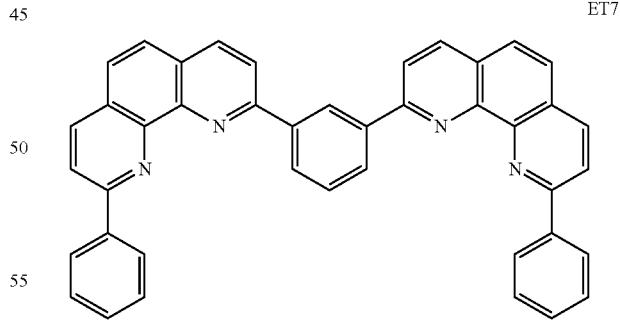

ET8

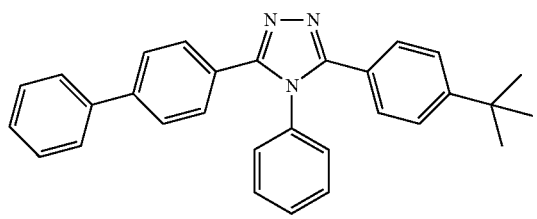

ET9
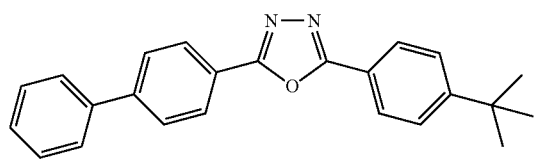
ET10
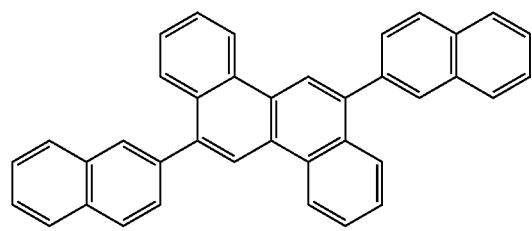
ET11
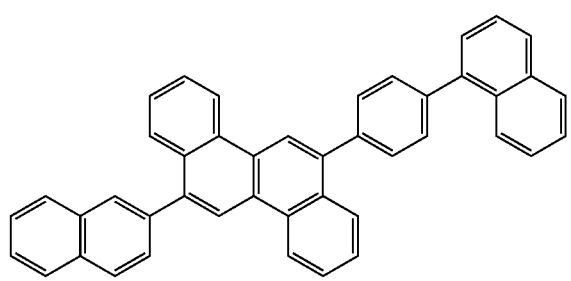
ET12
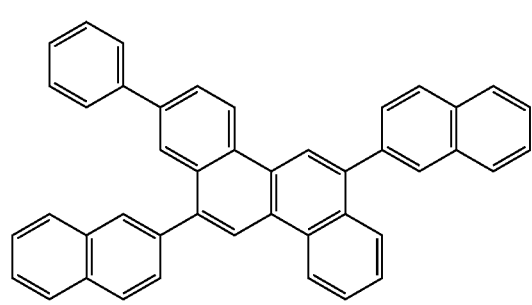
ET13
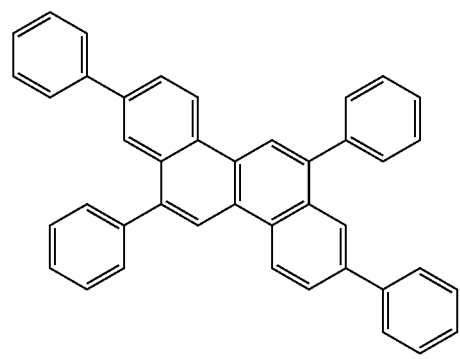
ET14
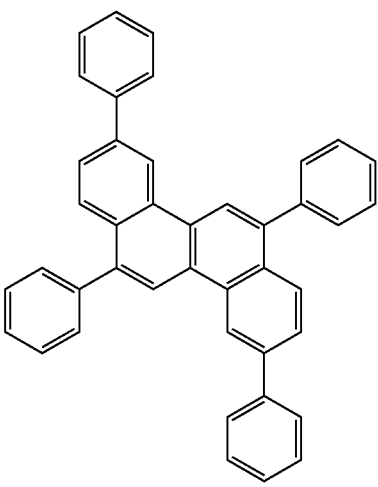
ET15
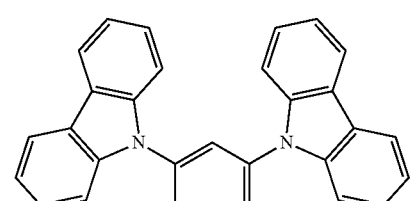
ET16
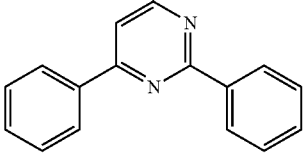

ET17
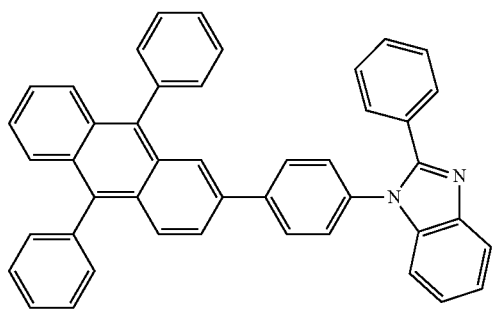

ET18
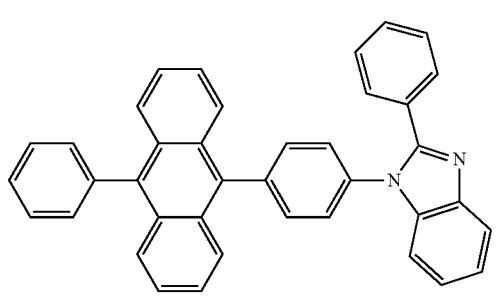

ET19
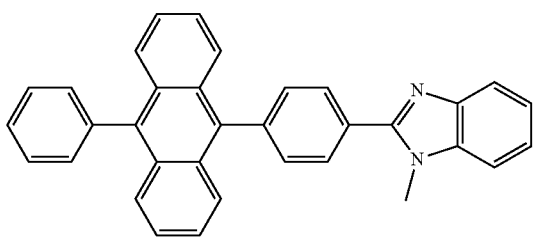

ET20
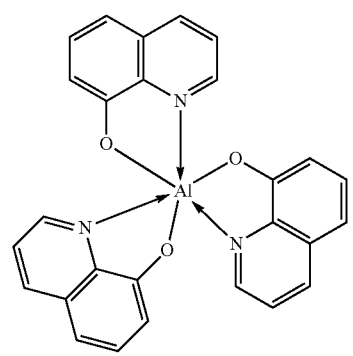

ET21
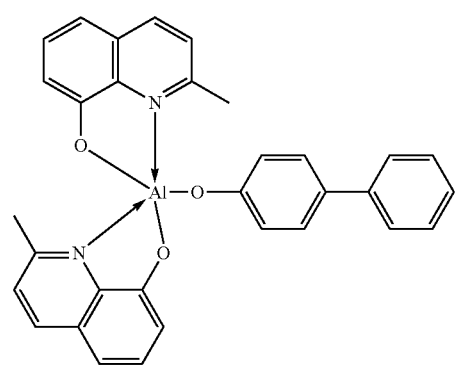

ET22
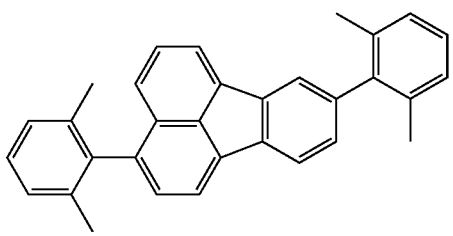

ET23
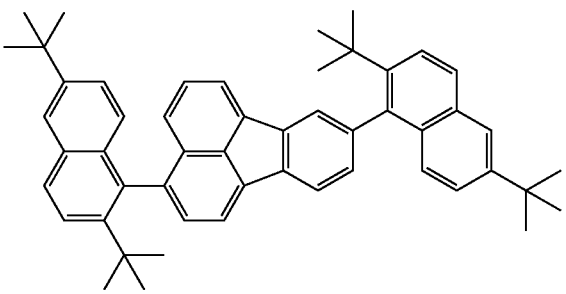

Configuration of Organic Light-Emitting Element

An organic light-emitting element is obtained by providing an anode, an organic compound layer, and a cathode on a substrate. For example, a protective layer and a color filter may be disposed on the cathode. In the case where a color filter is disposed, a planarizing layer may be formed in advance.

Examples of the substrate include quartz, glass, silicon wafers, resins, and metals. The substrate includes switching elements, such as transistors, and conductive lines thereon and may further include an insulating layer thereon. The material of the insulating layer is not limited as long as a contact hole can be formed in order to establish electrical connection between the anode and a conductive line and insulation from an unconnected conductive line can be achieved. Examples of the material of the insulating layer include resins such as polyimide, silicon oxide, and silicon nitride.

The material of the anode preferably has a work function that is as high as possible. Examples of the material of the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Examples thereof further include conductive polymers such as polyaniline, polypyrrole, and polythiophene.

These electrode materials may be used alone or in combination of two or more thereof. The anode may be formed of a single layer or a plurality of layers.

When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the transparent electrode is not limited thereto. Photolithography can be used for forming the electrodes.

In contrast, the material of the cathode preferably has a low work function. Examples of the material of the cathode include alkali metals such as lithium; alkaline earth metals such as calcium; elemental metals such as aluminum, titanium, manganese, silver, lead, and chromium; and mixtures containing these metals. Alloys of these elemental metals can also be used. For example, magnesium-silver, aluminum-lithium, aluminum-magnesium, silver-copper, and zinc-silver can be used. Metal oxides such as indium tin oxide (ITO) can also be used. These electrode materials may be used alone or in combination of two or more thereof. The cathode may be formed of a single layer or multiple layers.

The form of the cathode is not particularly limited. The cathode may be a conductive oxide layer made of ITO or the like to provide a top-emission element. Alternatively, the cathode may be a reflection electrode made of aluminum (Al) or the like to provide a bottom-emission element. The method for forming the cathode is not particularly limited. For example, DC and AC sputtering methods may be used because good film coverage is achieved to easily reduce the resistance.

After the formation of the cathode, a sealing member (not illustrated) may be disposed. For example, a glass plate provided with a moisture absorbent may be bonded to the cathode. Thus, permeation of water or the like in an organic EL layer can be suppressed to suppress the occurrence of display defects. In another embodiment, a passivation film made of silicon nitride or the like may be disposed on the cathode to suppress permeation of water or the like in an organic EL layer. For example, after the formation of the cathode, the resulting substrate may be transferred to another chamber without breaking the vacuum, and a silicon nitride film having a thickness of 2 µm may be formed by a CVD method to provide a protective layer.

A color filter may be disposed on each pixel. For example, color filters each having a size corresponding to the pixel size may be formed on another substrate, and this substrate may be bonded to the substrate having organic EL elements thereon. Alternatively, a color filter may be formed by patterning on a sealing film made of silicon oxide or the like using photolithography.

The organic compound layers (such as a hole injection layer, a hole transport layer, an electron blocking layer, a light-emitting layer, a hole blocking layer, an electron transport layer, and an electron injection layer) that form an organic light-emitting element according to the present embodiment are formed by the following method.

The organic compound layers that form an organic light-emitting element according to the present embodiment can be formed by employing a dry process such as a vacuum vapor deposition method, an ionized vapor deposition method, sputtering, or plasma. Alternatively, instead of the dry process, it is also possible to employ a wet process in which an organic compound is dissolved in a suitable solvent, and a layer is formed by a known coating method (such as spin coating, dipping, a casting method, a Langmuir-Blodgett (LB) method, or an ink jet method).

When a layer is formed by, for example, a vacuum vapor deposition method or a solution coating method, crystallization is unlikely to occur, and the resulting layer has good stability with time. When a layer is formed by a coating method, the layer may be formed by using a suitable binder resin in combination.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins.

These binder resins may be used alone as a homopolymer or a copolymer or in combination as a mixture of two or more thereof. Furthermore, known additives such as a plasticizer, an oxidation inhibitor, and an ultraviolet absorbent may be optionally used in combination.

Applications of Organic Light-Emitting Element of the Embodiment

The organic light-emitting element according to the present embodiment can be used as a member of a display device or an illumination device. In addition, the organic light-emitting element may be used as, for example, an exposure light source of an electrophotographic image forming apparatus, a backlight of a liquid crystal display device, or a light-emitting device including a white light source having a color filter.

The display device may be an image information processing device that includes an image input unit in which image information from an area CCD, a linear CCD, a memory card, or the like is input and an information processing unit in which the input information is processed and that displays an input image on a display unit.

The display unit included in an imaging device or an ink jet printer may have a touch panel function. The touch panel function may be operated by using infrared, an electrostatic capacitance, a resistive film, or electromagnetic induction, and the operation method is not particularly limited. The display device may be used as a display unit of a multifunctional printer.

Figure 2:
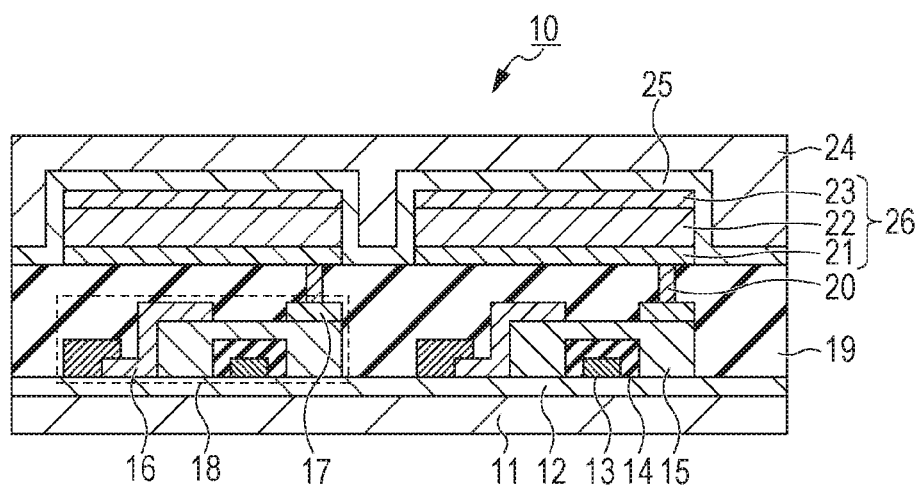
FIG. 2 is a schematic sectional view illustrating an example of a display device including organic light-emitting elements according to the present embodiment and transistors that are electrically connected to the organic light-emitting elements.

Next, a display device according to the present embodiment will be described with reference to the drawings. FIG. 2 is a schematic sectional view illustrating an example of a display device including organic light-emitting elements and TFT elements connected to the organic light-emitting elements. The TFT elements are each an example of an active element.

A display device 10 in FIG. 2 includes a substrate 11 made of, for example, glass and a moisture-proof film 12 that is disposed on the substrate 11 and that protects a TFT element or an organic compound layer. A metal gate electrode 13, a gate insulating film 14, and a semiconductor layer 15 are provided.

A TFT element 18 includes the semiconductor layer 15, a drain electrode 16, and a source electrode 17. An insulating film 19 is disposed on the TFT element 18. An anode 21 that forms an organic light-emitting element 26 and the source electrode 17 are connected to each other through a contact hole 20.

The form of electrical connection between electrodes (anode and cathode) included in the organic light-emitting element and electrodes (source electrode and drain electrode) included in the TFT is not limited to the form illustrated in FIG. 2. Specifically, either the anode or the cathode is electrically connected to either the source electrode or the drain electrode of the TFT element.

In the display device 10 in FIG. 2, an organic compound layer 22 is illustrated as if the organic compound layer 22 is formed of a single layer. Alternatively, the organic compound layer 22 may be formed of a plurality of layers. A first protective layer 24 and a second protective layer 25 that suppress deterioration of the organic light-emitting element 26 are disposed on a cathode 23.

In the display device 10 in FIG. 2, transistors are used as switching elements. Alternatively, MIM elements may be used as switching elements instead of the transistors.

The transistors used in the display device 10 in FIG. 2 are not limited to transistors using a single-crystal silicon wafer. Alternatively, the transistors may be thin-film transistors having an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. Thin-film transistors are also referred to as TFT elements.

The transistors included in the display device 10 in FIG. 2 may be formed in a substrate such as a Si substrate. Herein, the expression "formed in a substrate" means that transistors are produced by processing a substrate, such as a Si substrate, itself. That is, having transistors in a substrate can also be considered that a substrate and transistors are integrally formed.

Whether or not transistors are disposed in a substrate is selected depending on the level of resolution. For example, in the case of a size of 1 inch and a resolution of about QVGA, the transistor may be disposed in a Si substrate.

Figure 3:
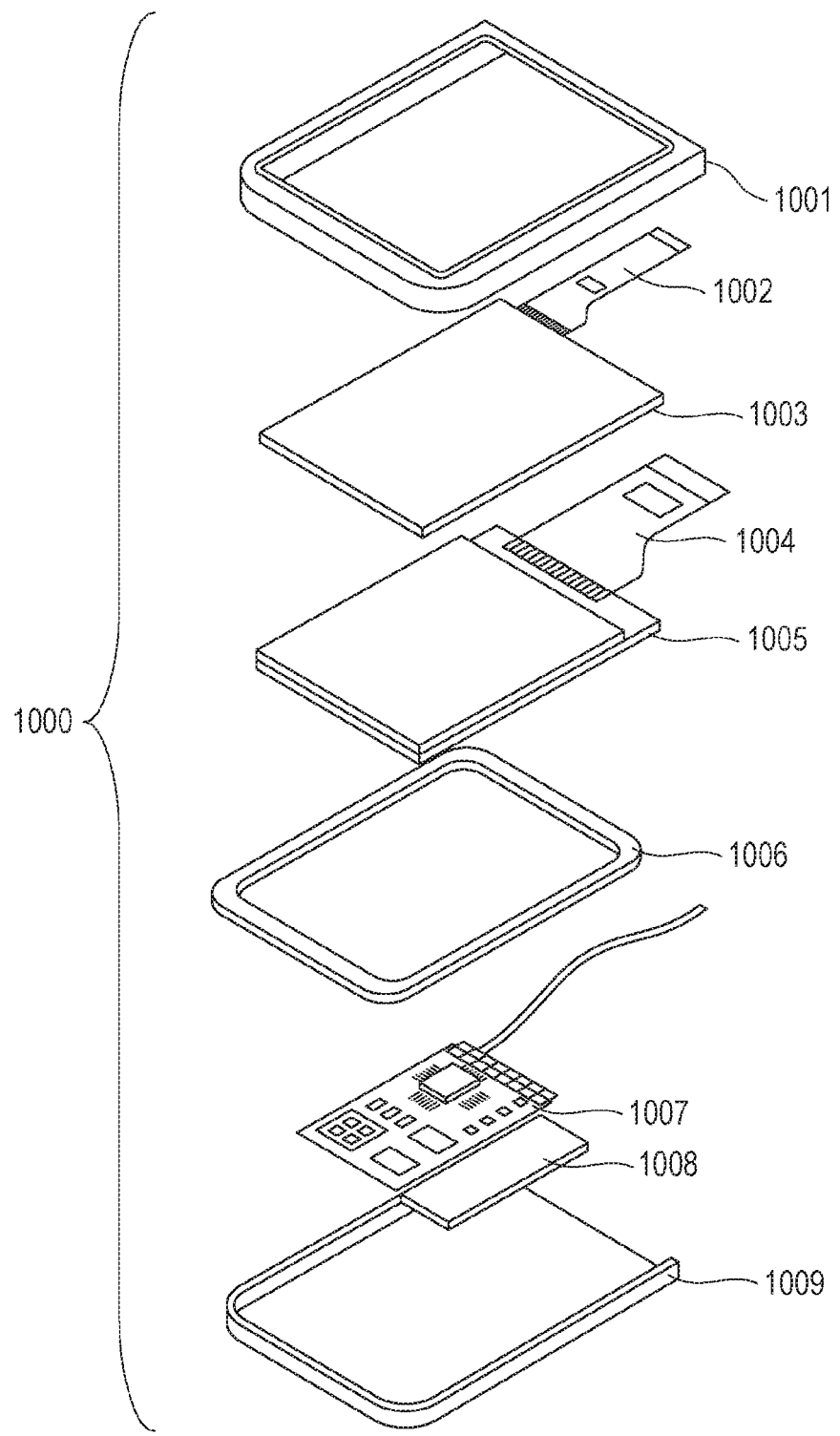
FIG. 3 is a schematic view illustrating an example of a display device according to the present embodiment.

FIG. 3 is a schematic view illustrating an example of a display device according to the present embodiment. A display device 1000 may include an upper cover 1001, a lower cover 1009, and a touch panel 1003, a display panel 1005, a frame 1006, a printed circuit board 1007, and a battery 1008 that are disposed between the upper cover 1001 and the lower cover 1009. The touch panel 1003 and the display panel 1005 are connected to flexible printed circuits (FPC) 1002 and 1004, respectively. Transistors are printed on the printed circuit board 1007. The battery 1008 is not necessarily provided unless the display device is a mobile device. Even when the display device is a mobile device, the battery 1008 is not necessarily disposed at the position illustrated in the figure.

The display device according to the present embodiment may be used as a display unit of an imaging device including an optical unit having a plurality of lenses and an imaging element that receives light that has passed through the optical unit. The imaging device may include a display unit that displays information obtained by the imaging element. The display unit may be a display unit exposed to the outside of the imaging device or a display unit disposed in a viewfinder. The imaging device may be a digital camera or a digital camcorder.

Figure 4A:
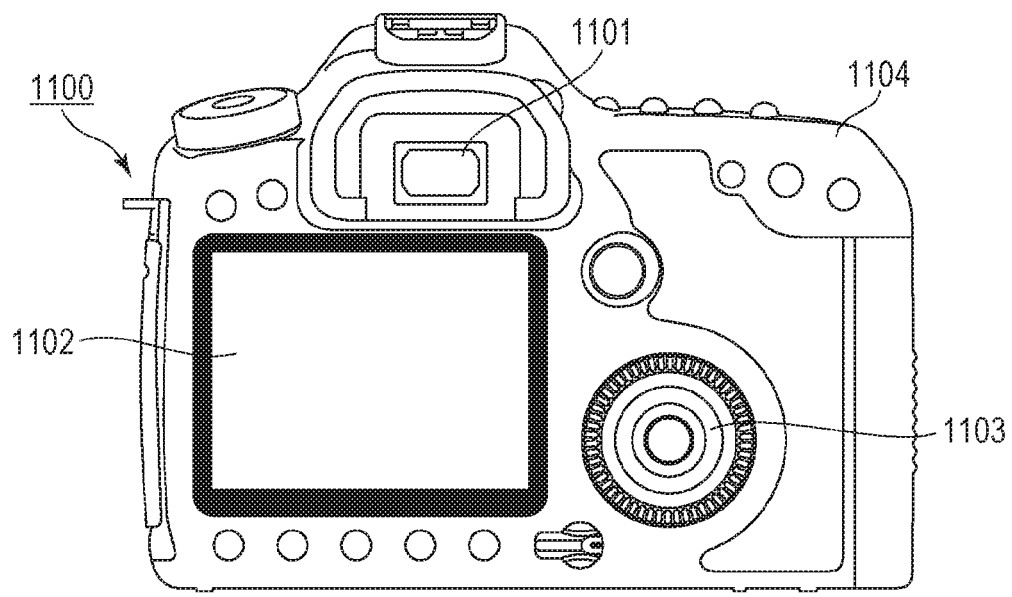
FIG. 4A is a schematic view illustrating an example of an imaging device according to the present embodiment.

FIG. 4A is a schematic view illustrating an example of an imaging device according to the present embodiment. An imaging device 1100 may include a viewfinder 1101, a rear display 1102, an operation unit 1103, and a housing 1104. The viewfinder 1101 may include the display device according to the present embodiment. In such a case, the display device may display not only an image to be captured but also, for example, environmental information and imaging instructions. The environmental information may include, for example, the intensity of external light, the direction of external light, the moving speed of a subject to be captured, and the possibility that the subject is hidden by an object.

Since the suitable timing for taking an image is a very short period of time, it is desirable to display information as quickly as possible. Accordingly, the display device including the organic light-emitting element according to the present disclosure is preferably used. This is because the organic light-emitting element has a high response speed. The display device including the organic light-emitting element is more suitable than liquid crystal display devices for use in apparatuses for which a high display speed is required.

The imaging device 1100 includes an optical unit (not illustrated). The optical unit has a plurality of lenses and forms an image on an imaging element disposed in the housing 1104. The focus can be adjusted by adjusting the relative positions of the plurality of lenses. This operation may be automatically performed.

The display device according to the present embodiment may include red, green, and blue color filters. The red, green, and blue color filters may be arranged in a delta array.

The display device according to the present embodiment may be used in a display unit of a mobile terminal. In such a case, the display unit may have both a display function and an operational function. Examples of the mobile terminal include mobile phones, such as smartphones, tablet computers, and head-mounted displays.

Figure 4B:
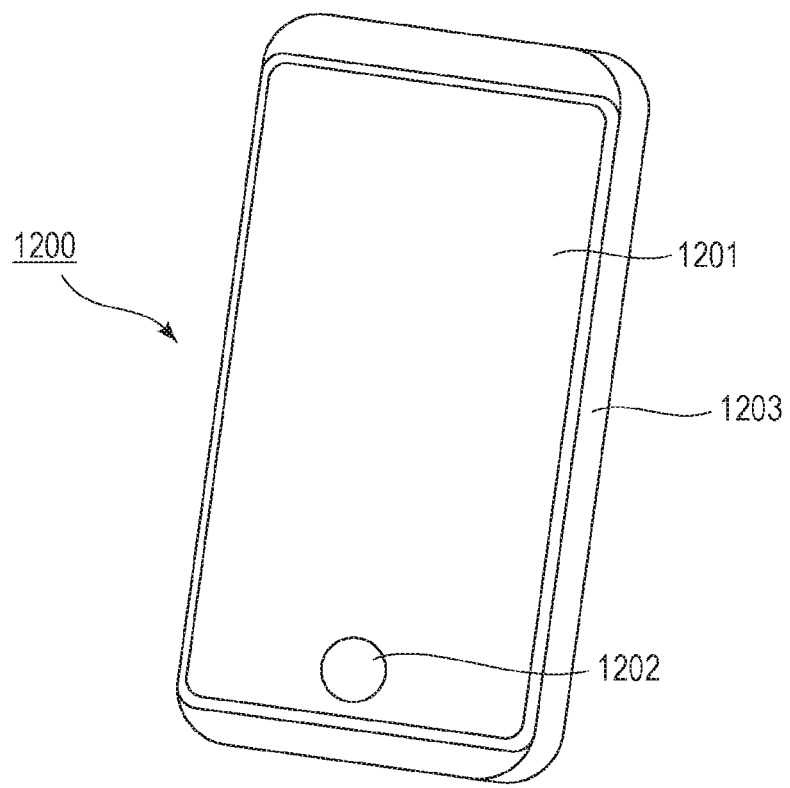
FIG. 4B is a schematic view illustrating an example of a mobile device according to the present embodiment.

FIG. 4B is a schematic view illustrating an example of an electronic device according to the present embodiment. An electronic device 1200 include a display unit 1201, an operation unit 1202, and a housing 1203. The housing 1203 may include therein circuits, a printed board having the circuits, a battery, and a communication unit. The operation unit 1202 may be a button or a touch-panel response unit. The operation unit 1202 may be a biometric authentication unit configured to, for example, recognize the fingerprint and release the lock. An electronic device including a communication unit may be referred to as a communication device.

Figure 5A:
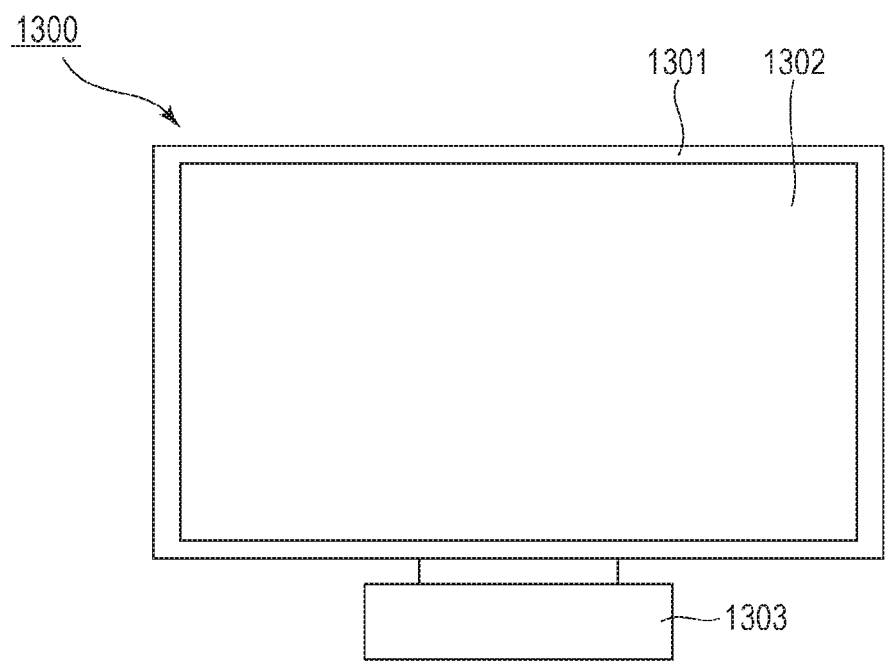
FIG. 5A is a schematic view illustrating an example of a display device according to the present embodiment.
Figure 5B:
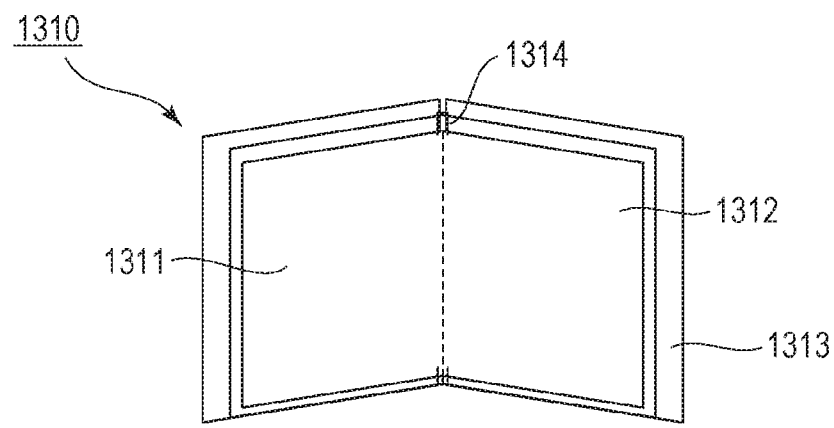
FIG. 5B is a schematic view illustrating an example of a foldable display device.

FIGS. 5A and 5B are schematic views each illustrating an example of a display device according to the present embodiment. FIG. 5A illustrates a display device such as a television monitor or a personal computer (PC) monitor. A display device 1300 includes a frame 1301 and a display unit 1302. The display unit 1302 may include the light-emitting element according to the present embodiment.

The display device 1300 further includes a base 1303 that supports the frame 1301 and the display unit 1302. The base 1303 is not limited to the form illustrated in FIG. 5A. Alternatively, the lower side of the frame 1301 may also function as the base.

The frame 1301 and the display unit 1302 may be curved. The radius of curvature thereof may be in a range of 5,000 mm or more and 6,000 mm or less.

FIG. 5B is a schematic view illustrating another example of a display device according to the present embodiment. A display device 1310 illustrated in FIG. 5B is configured to be foldable and is a so-called foldable display device. The display device 1310 has a first display unit 1311, a second display unit 1312, a housing 1313, and a folding point 1314. Each of the first display unit 1311 and the second display unit 1312 may include the light-emitting element accordion to the present embodiment. The first display unit 1311 and the second display unit 1312 may be a single display device without a joint. The first display unit 1311 and the second display unit 1312 can be separated from each other in the folding point 1314. The first display unit 1311 and the second display unit 1312 may display images that are different from each other. Alternatively, one image may be displayed on a set of the first display unit 1311 and the second display unit 1312.

Figure 6A:
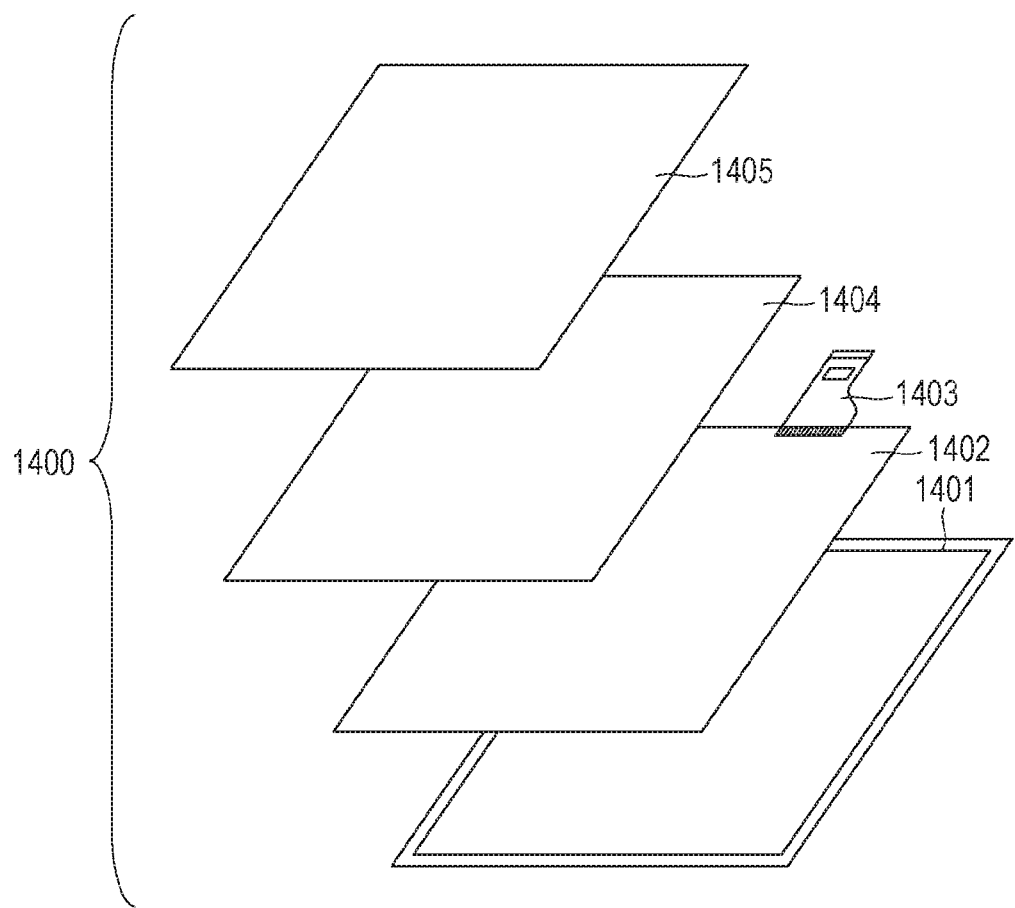
FIG. 6A is a schematic view illustrating an example of an illumination device according to the present embodiment.

FIG. 6A is a schematic view illustrating an example of an illumination device according to the present embodiment. An illumination device 1400 may include a housing 1401, a light source 1402, a circuit board 1403, an optical film 1404, and a light diffusion unit 1405. The light source 1402 may include the organic light-emitting element according to the present embodiment. The optical film 1404 may be a film that improves the color rendering properties of the light source 1402. The light diffusion unit 1405 effectively diffuses light emitted from the light source 1402 and allows the light to reach a wide region, for example, for lighting up. The optical film 1404 and the light diffusion unit 1405 may be disposed on the light-emitting side of illumination. A cover may be optionally disposed on an outermost portion.

The illumination device is, for example, a device that illuminates a room. The illumination device may emit light of white, natural white, or any other color from blue to red. The illumination device may include a light modulation circuit configured to modulate the light. The illumination device may include the organic light-emitting element according to the present disclosure and a power supply circuit connected to the organic light-emitting element. The power supply circuit is a circuit configured to convert an alternating voltage to a direct voltage. The white has a color temperature of 4,200 K, and the natural white has a color temperature of 5,000 K. The illumination device may include a color filter.

The illumination device according to the present embodiment may include a heat dissipation unit. The heat dissipation unit dissipates heat in the device to the outside of the device and may be made of, for example, a metal having a high specific heat or liquid silicon.

Figure 6B:
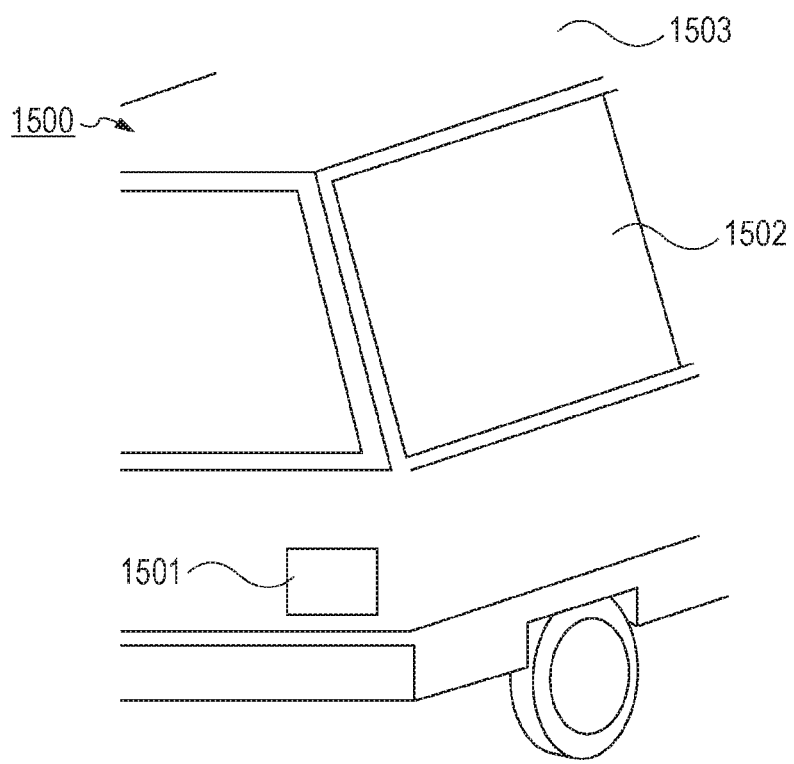
FIG. 6B is a schematic view illustrating an automobile which is an example of a moving object according to the present embodiment.

FIG. 6B is a schematic view of an automobile which is an example of a moving object according to the present embodiment. The automobile includes a tail lamp which is an example of a lighting fixture. An automobile 1500 includes a tail lamp 1501, and the tail lamp 1501 may light up when, for example, the brakes are applied.

The tail lamp 1501 may include the organic light-emitting element according to the present embodiment. The tail lamp 1501 may include a protective member that protects the organic light-emitting element. The protective member may be made of any material as long as the strength of the protective member is high to a certain extent, and the protective member is transparent. The protective member may be made of polycarbonate or the like. The polycarbonate may be mixed with a furandicarboxylic acid derivative, an acrylonitrile derivative, or the like.

The automobile 1500 may include a car body 1503 and a window 1502 attached to the car body 1503. The window may be a transparent display unless it is a window for checking of the front and rear of the automobile. The transparent display may include the organic light-emitting element according to the present embodiment. In such a case, the members such as electrodes of the organic light-emitting element are made of transparent materials.

The moving object according to the present embodiment may be a ship, aircraft, a drone, or the like. The moving object may include a body and a lighting fixture disposed on the body. The lighting fixture may emit light for notifying the position of the body. The lighting fixture includes the organic light-emitting element according to the present embodiment.

In the organic light-emitting element according to the present embodiment, the emission luminance is controlled by a TFT which is an example of a switching element. Accordingly, when a plurality of such organic light-emitting elements are arranged in a plane, an image can be displayed by controlling the emission luminance of each of the organic light-emitting elements. The switching element according to the present embodiment is not limited to a TFT. The switching element may be a transistor formed of low-temperature polysilicon or an active matrix driver formed on a substrate or in a substrate such as a Si substrate. Whether on a substrate or in a substrate is selected depending on the level of resolution. For example, in the case of a size of 1 inch and a resolution of about QVGA, organic light-emitting elements may be disposed on a Si substrate. By driving the display device including the organic light-emitting elements according to the present embodiment, an image having good image quality can be stably displayed for a long time.

EXAMPLES

The present disclosure will now be described by way of Examples. The present disclosure is not limited to the Examples.

Example 1: Synthesis of Exemplary Compound A3

Synthesis of Compound E6

Compound E6 was synthesized by the following scheme.

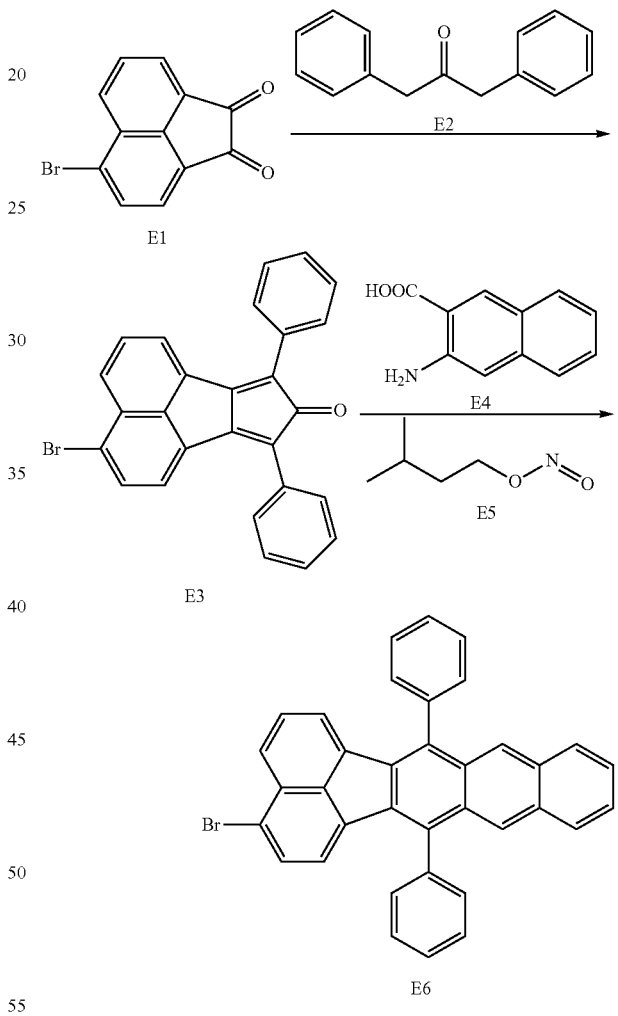

Compound E3 was synthesized in accordance with the synthesis method described in PTL 1. Furthermore, the following reagents were placed in a 200-mL recovery flask.

Compound E3: 4.1 g (9.5 mmol)
Compound E4: 2.1 g (11.0 mmol)
Isoamyl nitrite: 1.3 g (11.0 mmol)
Toluene: 100 mL The resulting reaction solution was heated in nitrogen at 95° C. for three hours under stirring. After the completion of the reaction, the solvent was distilled off under reduced pressure. The resulting solid was purified with a silica gel column (chloroform:heptane=1:3) to obtain 4.2 g of compound E6 (yield: 82%).

Synthesis of Compound E13

Compound E13 was synthesized in accordance with the synthesis scheme described in the present embodiment. Specifically, the synthesis was conducted in accordance with the following scheme.

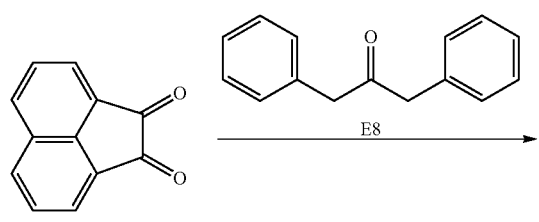

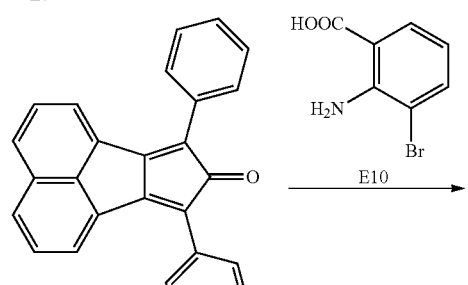

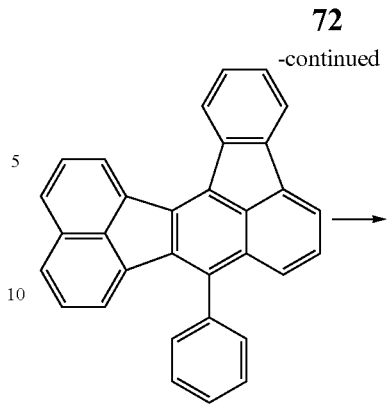

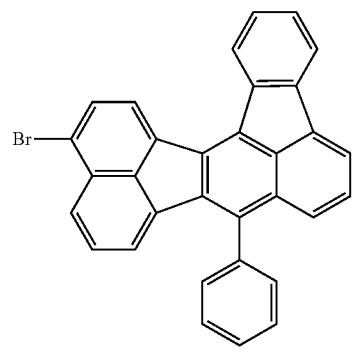

Synthesis of Compound E14

Compound E14 was synthesized by the following scheme.

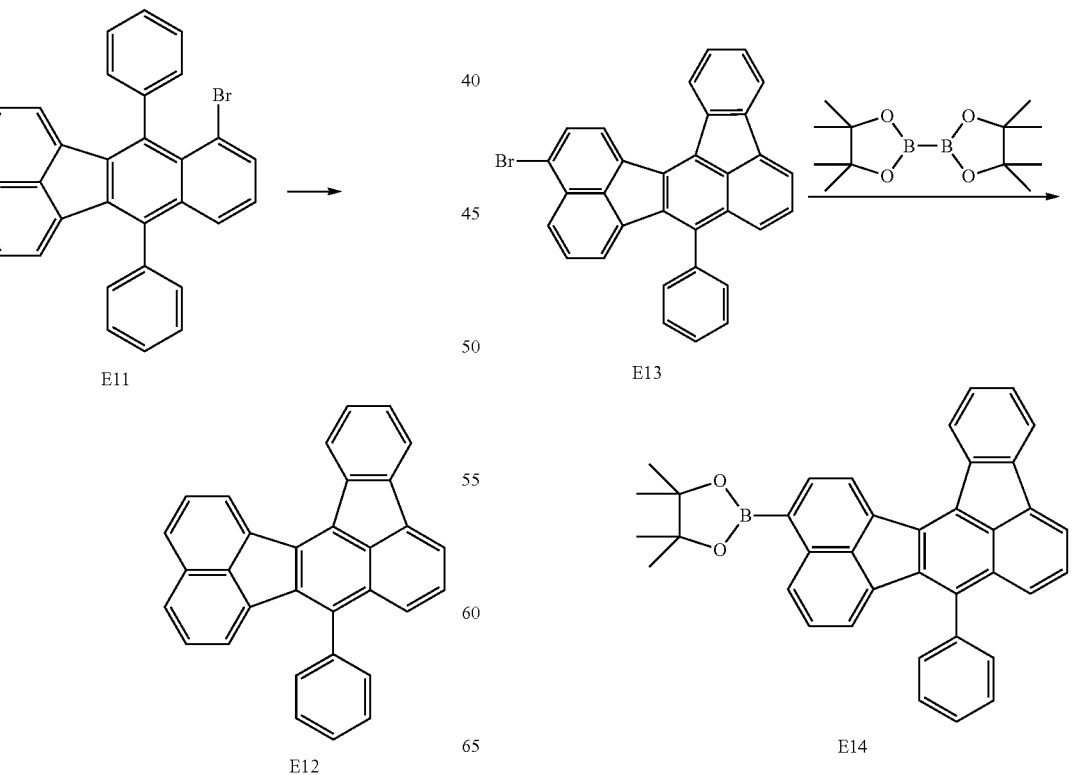

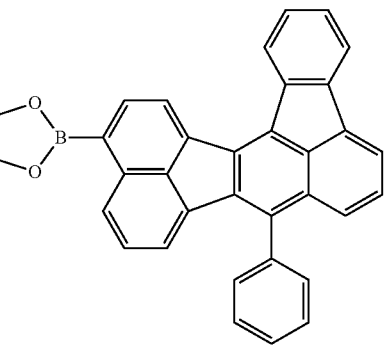

The following reagents were placed in a 100-mL recovery flask.
Compound E13: 2.4 g (5.0 mmol)
Bis(pinacolato)diboron: 1.3 g (5.0 mmol)
[1,1'-Bis(diphenylphosphino)ferrocene]palladium(II) dichloride dichloromethane adduct: 0.33 g (0.41 mmol)
Potassium acetate: 1.3 g (13.0 mmol)
1,4-Dioxane: 50 mL The resulting reaction solution was heated and refluxed in nitrogen for five hours under stirring. After the completion of the reaction, the solvent was distilled off under reduced pressure. The resulting solid was purified with a silica gel column (chloroform:heptane=2:1) to obtain 1.8 g of compound E14 (yield: 70%).

Synthesis of Exemplary Compound A3

Exemplary compound A3 was synthesized in accordance with the following scheme.

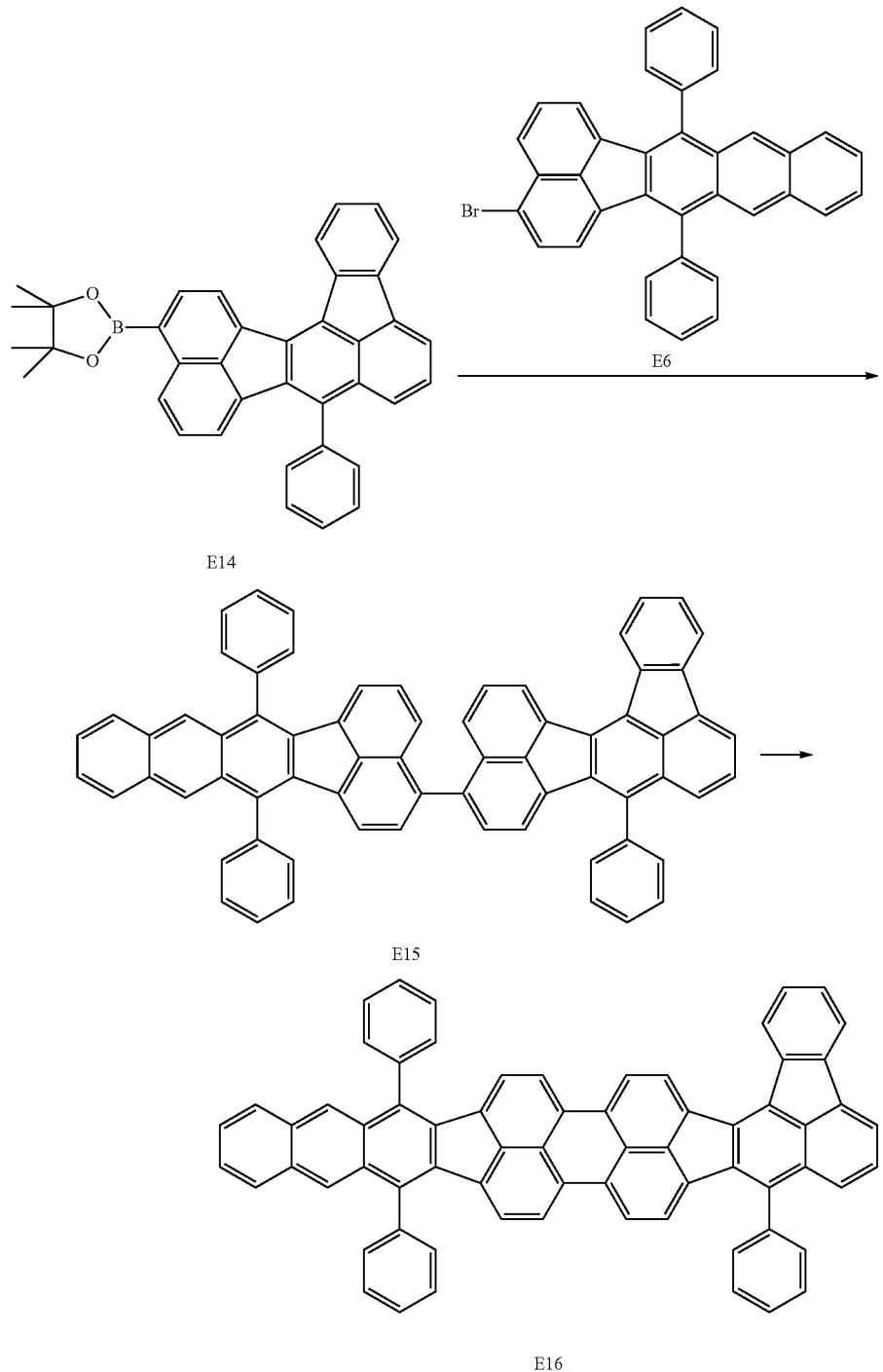

The following reagents and solvents were placed in a 100-mL recovery flask.
Compound E6: 1.6 g (3 mmol)
Compound E14: 1.6 g (3 mmol)
Pd(PPh$_3$)$_4$: 0.6 g
Toluene: 100 mL
Ethanol: 10 mL
2M-Aqueous sodium carbonate solution: 30 mL Next, the resulting reaction solution was heated to 80° C. in a nitrogen stream and stirred at this temperature (80° C.) for eight hours. After the completion of the reaction, ethanol was added to the resulting reaction solution to precipitate a crystal. The crystal was then separated by filtration and sequentially dispersed and washed in water, ethanol, and heptane. Next, the resulting crystal was dissolved in chlorobenzene under heating, subsequently subjected to hot filtration, and then recrystallized. As a result, 1.9 g of compound E15, which was a red compound, was obtained (yield: 75%).

The following reagents and solvent were placed in a 500-mL reaction container.
Compound E15: 1.7 g (2 mmol)
Trifluoroacetic acid: 20 mL
Methylene chloride: 150 mL Next, the following reagent was placed in the reaction container in a water bath.
BF$_3$.OEt: 4 mL Next, after the reaction solution was stirred for about 10 minutes, 1.0 g of 2,3-dichloro-5,6-dicyano-p-benzoquinone (DDQ) was placed in the reaction solution. Subsequently, after the reaction solution was stirred for 10 minutes, 1.0 g of ferrocene was placed in the reaction solution in a water bath at 20° C. After stirring was conducted for about five minutes, 150 mL of methanol was added. A red precipitate generated at this time was filtered to obtain a red solid. Next, the solid was dissolved in chlorobenzene and recrystallized with heptane. As a result, 1.1 g of exemplary compound A3 was obtained in the form of a blackish red crystal (yield: 65%).

Exemplary compound A3 was subjected to mass spectrometry by using a matrix assisted laser desorption/ionization time-of-flight mass spectrometer (MALDI-TOF-MS) (Autoflex LRF manufactured by Bruker Corporation).
MALDI-TOF-MS
Actual measured value: m/z=853
Calculated value: C$_{58}$H$_{30}$=853

Examples 2 to 13: Synthesis of Exemplary Compounds

Exemplary compounds shown in Table 5 below were synthesized as in Example 1 except that the raw materials E2, E4, and E8 in Example 1 were changed to a raw material 1, a raw material 2, and a raw material 3, respectively. Table 5 further shows the actual measured value m/z of the results of mass spectrometry performed as in Example 1.

TABLE 5

| Example | Exemplary compound | Raw material 1 | Raw material 2 | Raw material 3 | m/z |
|---|---|---|---|---|---|
| Example 2 | B2 | (3,5-di-tert-butylphenyl)-substituted dibenzyl ketone | 3-amino-2-naphthoic acid | 1,3-diphenylacetone | 1077 |
| Example 3 | B3 | (3,5-di-tert-butylphenyl)-substituted dibenzyl ketone | 3-amino-2-naphthoic acid | 1-(3,5-di-tert-butylphenyl)-3-phenylacetone | 1089 |

TABLE 5-continued
| Example | Exemplary compound | Raw material 1 | Raw material 2 | Raw material 3 | m/z |
|---|---|---|---|---|---|
| Example 4 | 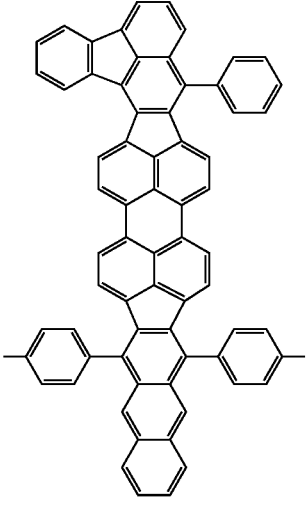 B14 | 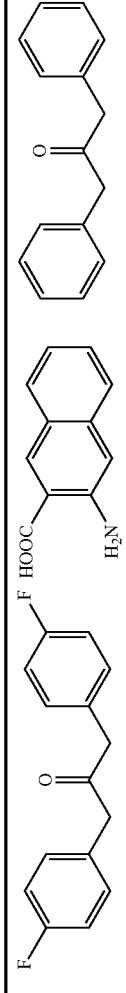 | 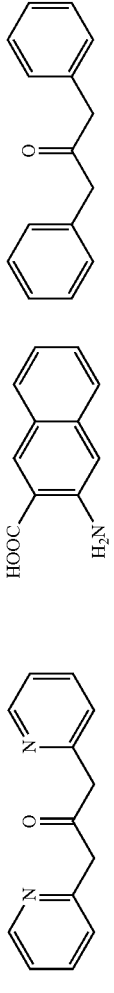 |  | 889 |
| Example 5 | 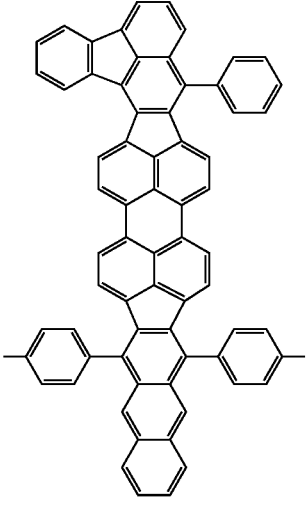 B16 | 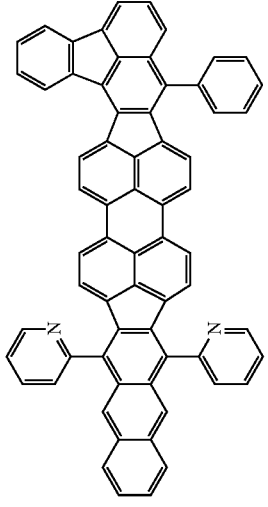 | 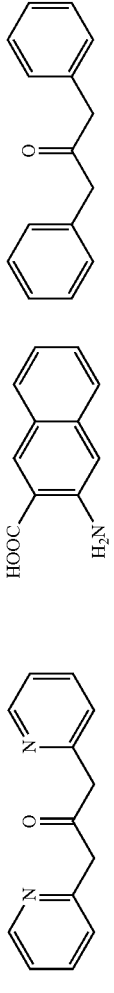 |  | 855 |

TABLE 5-continued
| Example | Exemplary compound | Raw material 1 | Raw material 2 | Raw material 3 | m/z |
|---|---|---|---|---|---|
| Example 6 | B18 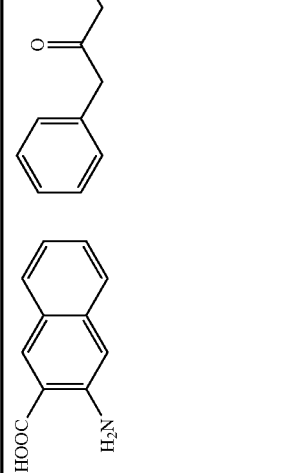 | 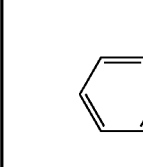 | 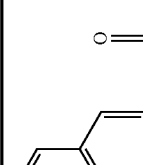 | 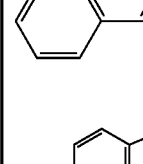 | 903 |
| Example 7 | B23 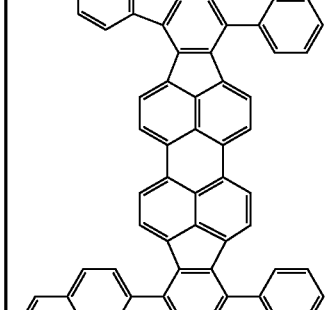 | 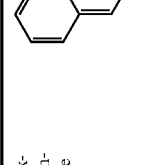 | 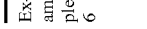 |  | 903 |

TABLE 5-continued

| Example | Exemplary compound | Raw material 1 | Raw material 2 | Raw material 3 | m/z |
|---|---|---|---|---|---|
| Example 8 | C1 | (2-methylbenzyl ketone) | 3-amino-2-naphthoic acid | dibenzyl ketone | 881 |
| Example 9 | C5 | (2,4-dimethylbenzyl ketone) | 3-amino-2-naphthoic acid | dibenzyl ketone | 909 |

TABLE 5-continued
| Example | Exemplary compound | Raw material 1 | Raw material 2 | Raw material 3 | m/z |
|---|---|---|---|---|---|
| Example 10 | 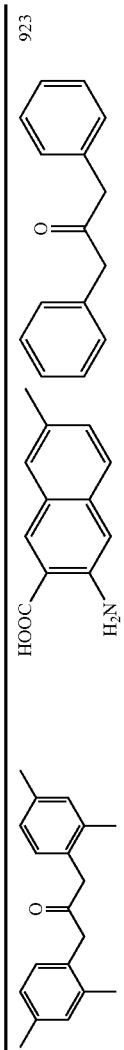 C9 | 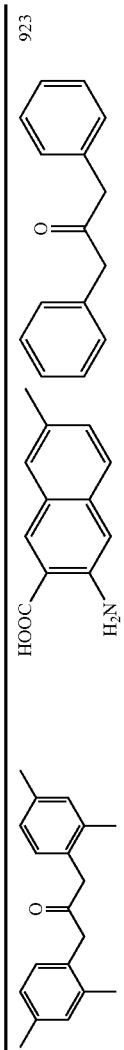 | 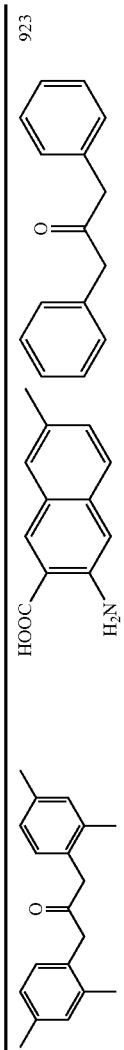 | 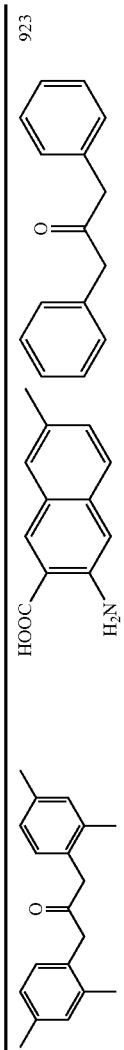 | 923 |
| Example 11 | 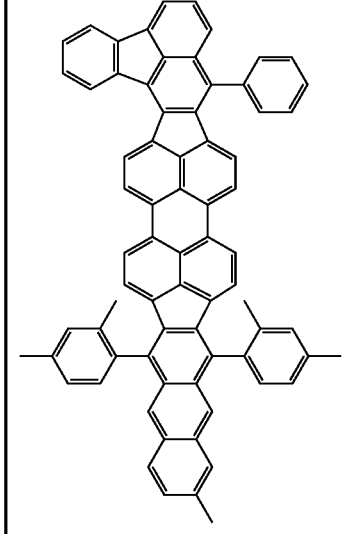 D1 | 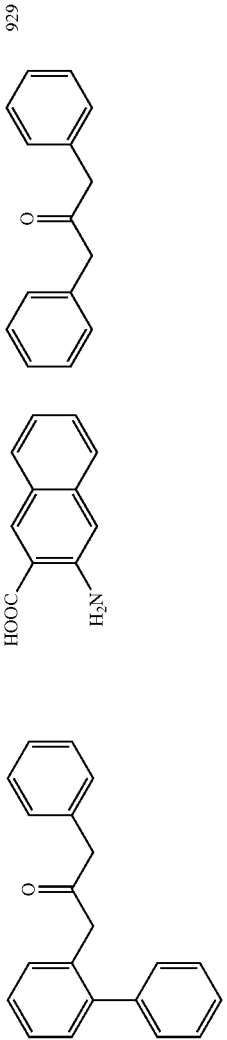 | 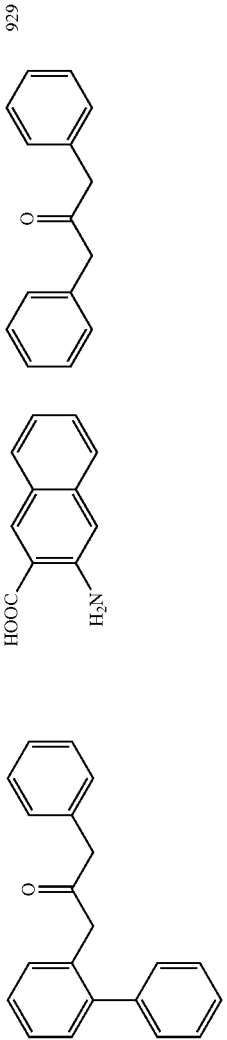 | 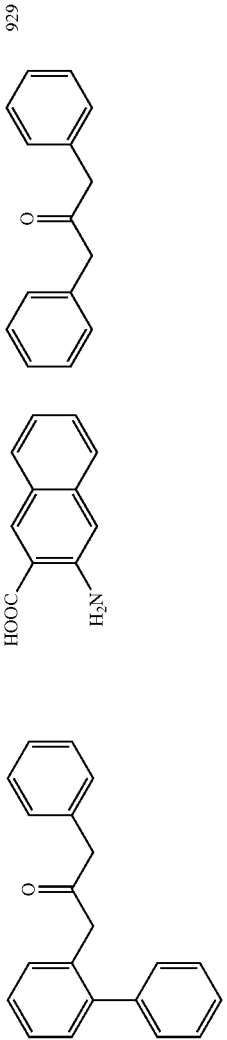 | 929 |
| Example 12 | 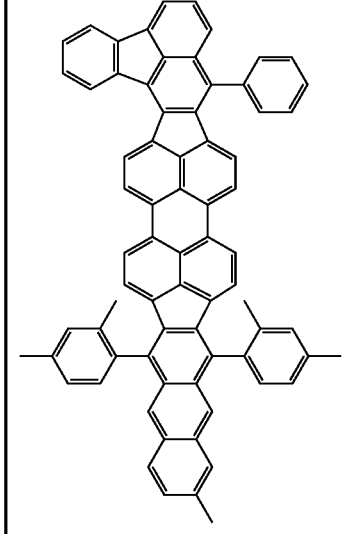 D3 | 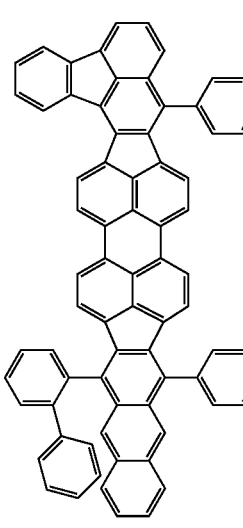 | 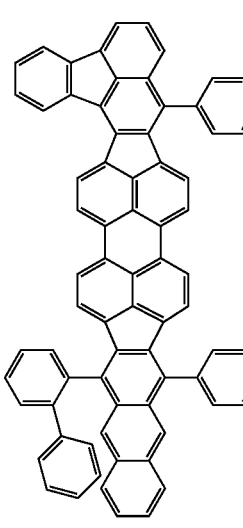 | 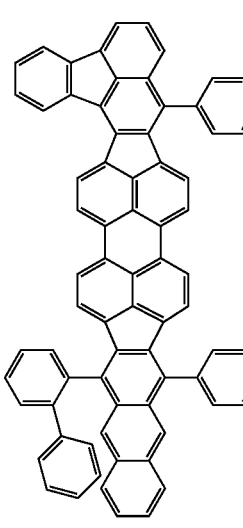 | 1005 |

TABLE 5-continued
| Example | Exemplary compound | Raw material 1 | Raw material 2 | Raw material 3 | m/z |
|---|---|---|---|---|---|
| Example 13 | 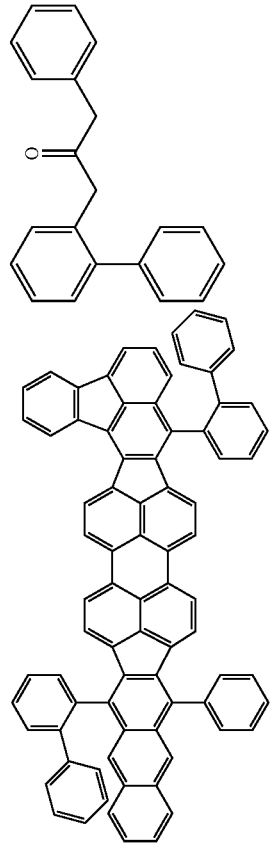<br>D4 | 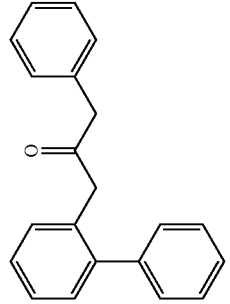 | 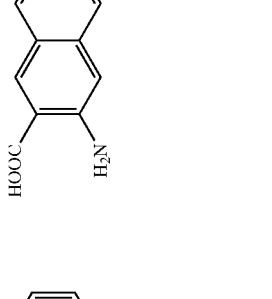 | 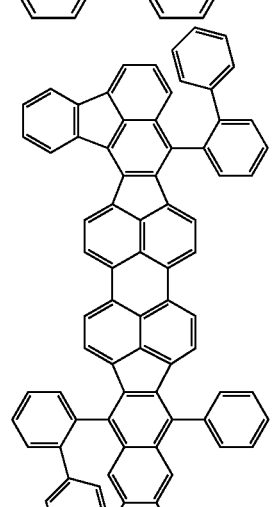 | 1005 |

Example 14

In the present Example, as the configuration shown in Table 6, a bottom-emission-type organic light-emitting element was produced in which an anode, a hole injection layer (HIL), a hole transport layer (HTL), an electron blocking layer (EBL), a light-emitting layer (EML), a hole blocking layer (HBL), an electron transport layer (ETL), an electron injection layer (EIL), and a cathode were sequentially formed on a substrate.

The light-emitting layer includes a host and a guest. The weight ratio of the host to the guest is host:guest=99.7 to 0.3.

First, ITO was deposited on a glass substrate, and the resulting ITO film was subjected to a desired pattering to form an ITO electrode (anode). At this time, the film thickness of the ITO electrode was 100 nm. After the preparation of an ITO substrate on which the ITO electrode was formed in this manner, an organic light-emitting element was produced by the process described below. The organic compound layers and the electrode layer (cathode) shown in Table 6 below were successively deposited on the ITO substrate by a resistance heating vacuum vapor deposition in a vacuum chamber at 1.33×10$^{-4}$ Pa. At this time, the area of the electrode (metal electrode layer, i.e., cathode) facing the anode was adjusted to 3 mm$^2$.

TABLE 6

| | Material | | Film thickness (nm) |
|---|---|---|---|
| Cathode | Al | | 100 |
| Electron injection layer | LiF | | 1 |
| Electron transport layer | ET5 | | 20 |
| Hole blocking layer | ET17 | | 20 |
| Light-emitting layer | Host | EM1 | 30 |
| | Guest | C1 | |
| Electron blocking layer | HT12 | | 15 |
| Hole transport layer | HT3 | | 30 |
| Hole injection layer | HT16 | | 5 |

Characteristics of the element obtained above were measured and evaluated. The light-emitting element had a maximum emission wavelength of 615 nm. Red light emission with a chromaticity of (X, Y)=(0.68, 0.32) was obtained. Regarding the specific measurement devices, current-voltage characteristics were measured with a microammeter 4140B manufactured by Hewlett-Packard, and the emission luminance was measured with BM7 manufactured by Topcon. Furthermore, a continuous driving test was conducted at a current density of 100 mA/cm$^2$, and the time taken for a rate of degradation of luminance to reach 5% was measured. According to the results, the time exceeded 500 hours.

Examples 15 to 21 and Comparative Example 1

Organic light-emitting elements were produced by the same method as that used in Example 14 except that the materials of the layers in Example 14 were changed to the compounds shown in Table 7 below. The characteristics of the elements obtained above were measured and evaluated as in Example 14. Table 7 shows the results of the measurement.

TABLE 7

| | | | | EML | | | | E.Q.E | Chromaticity coordinates of red |
|---|---|---|---|---|---|---|---|---|---|
| | HIL | HTL | EBL | Host | Guest | HBL | ETL | [%] | (x, y) |
| Example 15 | HT16 | HT2 | HT8 | EM17 | C5 | ET12 | ET2 | 4.7 | (0.68, 0.32) |
| Example 16 | HT16 | HT2 | HT8 | EM17 | D1 | ET12 | ET2 | 4.9 | (0.69, 0.31) |
| Example 17 | HT16 | HT2 | HT11 | EM16 | D1 | ET10 | ET2 | 4.8 | (0.69, 0.31) |
| Example 18 | HT16 | HT3 | HT8 | EM16 | D4 | ET12 | ET3 | 4.8 | (0.69, 0.31) |
| Example 19 | HT17 | HT3 | HT8 | EM18 | C2 | ET10 | ET3 | 4.7 | (0.68, 0.32) |
| Example 20 | HT17 | HT3 | HT8 | EM21 | D1 | ET12 | ET3 | 4.8 | (0.69, 0.31) |
| Example 21 | HT17 | HT3 | HT11 | EM16 | D4 | ET10 | ET3 | 4.7 | (0.69, 0.31) |
| Comparative Example 1 | HT16 | HT2 | HT11 | EM17 | Comparative compound 1-A | ET12 | ET2 | 4.4 | (0.67, 0.33) |

Referring to Table 7, the chromaticity coordinates of red in Comparative Example 1 are (0.67, 0.33). Comparing red light-emitting elements each including a red light-emitting layer containing an organic compound according to the present embodiment with the red light-emitting element including a red light-emitting layer containing comparative compound 1-A, the organic light-emitting elements according to the present embodiment have closer chromaticity coordinates (0.71, 0.29) in BT-2020 in the red range than the organic light-emitting element containing comparative compound 1-A, and thus can express a wider color gamut. This is due to the fact that the organic compounds according to the present embodiment emit red light at a longer wavelength.

Example 22

In the present Example, as the configuration shown in Table 8, a top-emission-type organic light-emitting element was produced in which an anode, a hole injection layer (HIL), a hole transport layer (HTL), an electron blocking layer (EBL), a first light-emitting layer (1st EML), a second light-emitting layer (2nd EML), a hole blocking layer (HBL), an electron transport layer (ETL), an electron injection layer (EIL), and a cathode were sequentially formed on a substrate.

The first light-emitting layer includes a first host, a first guest, and a third guest. The first guest is a red-light-emitting material, and the third guest is a green-light-emitting material. The weight ratio in the first light-emitting layer is first host:first guest:third guest=96.7:0.3:3.0.

The second light-emitting layer includes a second host and a second guest. The second guest is a blue-light-emitting material. The weight ratio in the second light-emitting layer is second host:second guest=99.4:0.6.

The cathode includes Ag and Mg. The weight ratio of the components that form the cathode is Ag:Mg=1:1.

Titanium (Ti) was deposited on a glass substrate by a sputtering method so as to have a thickness of 40 nm. The titanium film was patterned by photolithography to form an anode. At this time, the area of the electrode (metal electrode layer, i.e., cathode) facing the anode was adjusted to 3 mm$^2$.

Subsequently, the substrate having the anode after being cleaned and materials were placed in a vacuum vapor deposition apparatus (manufactured by ULVAC, Inc.), the apparatus was evacuated to $1.33 \times 10^{-4}$ Pa ($1 \times 10^{-6}$ Torr), and UV/ozone cleaning was then conducted. Subsequently, layers were formed so as to have the layer configuration shown in Table 8. Lastly, sealing was conducted in a nitrogen atmosphere.

TABLE 8

| | Material | | Film thickness (nm) |
|---|---|---|---|
| Cathode | Mg | | 10 |
| | Ag | | |
| Electron injection layer | LiF | | 1 |
| Electron transport layer | ET2 | | 30 |
| Hole blocking layer | ET12 | | 70 |
| Second light-emitting layer | Second host | EM1 | |
| | Second guest | BD5 | 10 |
| First light-emitting layer | First host | EM1 | |
| | First guest | C2 | 10 |
| | Third guest | GD8 | |
| Electron blocking layer | HT7 | | 15 |
| Hole transport layer | HT2 | | 30 |
| Hole injection layer | HT16 | | 5 |

Characteristics of the element obtained above were measured and evaluated. The element exhibited good white-light emission. The chromaticity coordinates of red after being transmitted through an RGB color filter was estimated from the resulting white light emission spectrum. The chromaticity coordinates of red were (0.69, 0.31).

Examples 23 to 27 and Comparative Example 2

Organic light-emitting elements were produced by the same method as that used in Example 22 except that the materials of the layers in Example 22 were changed to the compounds shown in Table 9 below. The characteristics of the elements obtained above were measured and evaluated as in Example 22. Table 9 shows the results of the measurement.

TABLE 9

| | First light-emitting layer | | | Second light-emitting layer | | Chromaticity coordinates of red (x, y) |
|---|---|---|---|---|---|---|
| | First host | First guest | Third guest | Second host | Second guest | |
| Example 23 | EM1 | D1 | GD8 | EM1 | BD6 | (0.70, 0.30) |
| Example 24 | EM4 | D1 | GD8 | EM4 | BD2 | (0.70, 0.30) |
| Example 25 | EM5 | C5 | GD4 | EM5 | BD4 | (0.69, 0.31) |
| Example 26 | EM1 | D4 | GD7 | EM1 | BD6 | (0.70, 0.30) |
| Example 27 | EM11 | C2 | GD9 | EM11 | BD6 | (0.69, 0.31) |
| Comparative Example 2 | EM1 | 1-A | GD4 | EM1 | BD6 | (0.68, 0.32) |

Referring to Table 9, the chromaticity coordinates of red in Comparative Example 2 are (0.68, 0.32). In contrast, the chromaticity coordinates of red of the white light-emitting elements each including a red light-emitting layer containing an organic compound according to the present embodiment are about (0.70, 0.31). The white light-emitting elements according to the present embodiment have closer chromaticity coordinates (0.71, 0.29) in BT-2020 in the red range than the organic light-emitting element containing comparative compound 1-A. These results show that the use of the organic light-emitting elements according to the present embodiment realizes a wider color reproduction range. This is due to the fact that the organic compounds according to the present embodiment emit red light at a longer wavelength.

According to the present disclosure, there is provided an organic compound having a basic skeleton that emits red light having a longer wavelength.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-152006 filed Aug. 10, 2018, which is hereby incorporated by reference herein in its entirety.

What is claimed is:

1. An organic compound represented by formula (1):

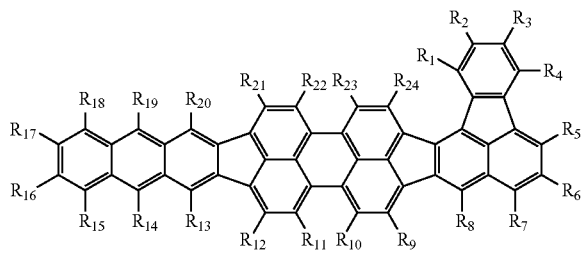

wherein $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein at least one of $R_1$ to $R_{24}$ in formula (1) is a phenyl group, and the phenyl group has a substituent at an ortho position of the phenyl group.

3. The organic compound according to claim 1, wherein at least two of $R_{13}$, $R_{14}$, $R_{19}$, and $R_{20}$ in formula (1) are each the substituted or unsubstituted aryl group.

4. The organic compound according to claim 1, wherein at least one of $R_{13}$ and $R_{14}$, at least one of $R_{19}$ and $R_{20}$, and $R_8$ in formula (1) are each the substituted or unsubstituted aryl group.

5. The organic compound according to claim 1,
wherein at least two of $R_{13}$, $R_{14}$, $R_{19}$, and $R_{20}$ in formula (1) are each a phenyl group,
the phenyl group has a substituent at least at an ortho position of the phenyl group, and
the substituent is selected from the group consisting of a halogen atom, a substituted or unsubstituted alkyl group, a substituted or unsubstituted aryl group, a substituted or unsubstituted heterocyclic group, and a cyano group.

6. The organic compound according to claim 5, wherein at least one of $R_{13}$ and $R_{14}$ and at least one of $R_{19}$ and $R_{20}$ are each a phenyl group, the phenyl group has a substituent at least at an ortho position of the phenyl group, and the substituent is selected from the group consisting of a halogen atom, a substituted or unsubstituted alkyl group, a substituted or unsubstituted aryl group, a substituted or unsubstituted heterocyclic group, and a cyano group.

7. An organic light-emitting element comprising:

a pair of electrodes; and an organic compound layer disposed between the pair of electrodes, wherein the organic compound layer includes the organic compound according to claim 1.

8. The organic light-emitting element according to claim 7, wherein the organic compound layer includes a light-emitting layer.

9. The organic light-emitting element according to claim 8, wherein the organic light-emitting element emits red light.

10. The organic light-emitting element according to claim 9, wherein the organic compound layer further includes another light-emitting layer stacked on the light-emitting layer, and the other light-emitting layer emits light of a color different from a color of light emitted from the light-emitting layer.

11. The organic light-emitting element according to claim 10, wherein the organic light-emitting element emits white light.

12. A display device comprising a plurality of pixels, wherein the plurality of pixels each include the organic light-emitting element according to claim 7 and a transistor connected to the organic light-emitting element.

13. The display device according to claim 12, comprising a color filter on a light-emitting side of each of the pixels.

14. An imaging device comprising:

an optical unit having a plurality of lenses;

an imaging element that receives light that has passed through the optical unit; and a display unit that displays an image, wherein the display unit displays an image captured by the imaging element, and the display unit includes the organic light-emitting element according to claim 7.

15. An electronic device comprising:

a housing;

a communication unit that communicates with an outside; and a display unit, wherein the display unit includes the organic light-emitting element according to claim 7.

16. An illumination device comprising:

a light source; and a light diffusion unit or an optical film, wherein the light source includes the organic light-emitting element according to claim 7.

17. A moving object comprising:

a body; and a lighting fixture disposed on the body, wherein the lighting fixture includes the organic light-emitting element according to claim 7.

* * * * *